United States Patent
Zhang et al.

(10) Patent No.: US 9,943,703 B2
(45) Date of Patent: Apr. 17, 2018

(54) SYSTEM AND METHOD FOR IRRADIATION THERAPY USING VOXEL BASED FUNCTIONAL MEASUREMENTS OF ORGANS AT RISK

(71) Applicants: Hao H. Zhang, Potomac, MD (US); Warren D. D'Souza, Timonium, MD (US); Nilesh N. Mistry, Cary, NC (US); Hamid R. Ghaffari, Gainesville, FL (US)

(72) Inventors: Hao H. Zhang, Potomac, MD (US); Warren D. D'Souza, Timonium, MD (US); Nilesh N. Mistry, Cary, NC (US); Hamid R. Ghaffari, Gainesville, FL (US)

(73) Assignee: THE UNIVERSITY OF MARYLAND, BALTIMORE, Baltimore, MD (US)

(*) Notice: Subject to any disclaimer, the term of this patent is extended or adjusted under 35 U.S.C. 154(b) by 436 days.

(21) Appl. No.: 14/811,207

(22) Filed: Jul. 28, 2015

(65) Prior Publication Data
US 2016/0023018 A1  Jan. 28, 2016

Related U.S. Application Data

(60) Provisional application No. 62/029,590, filed on Jul. 28, 2014.

(51) Int. Cl.
*A61N 5/00* (2006.01)
*A61N 5/10* (2006.01)
(Continued)

(52) U.S. Cl.
CPC ............ *A61N 5/1039* (2013.01); *A61B 5/055* (2013.01); *A61B 5/08* (2013.01); *A61B 5/743* (2013.01);
(Continued)

(58) Field of Classification Search
CPC .... A61N 5/103; A61N 5/1031; A61N 5/1039; A61B 6/00; A61B 6/032; A61B 6/037; A61B 6/52; A61B 6/5211; A61B 6/5235
(Continued)

(56) References Cited

U.S. PATENT DOCUMENTS 7,668,357 B2   2/2010  Keall et al.
2011/0058721 A1  3/2011  Zhang et al.
(Continued)

FOREIGN PATENT DOCUMENTS

WO   2009/132002 A9   10/2009
WO   2012/120422 A1   9/2012

OTHER PUBLICATIONS

Das, S., et al., "Feasibility of optimizing the dose distribution in lung tumors using fluorine-18-fluorodeoxyglucose positron emission tomography and single photon emission computed tomography guided dose prescriptions," Medical Physics, Jun. 2004, pp. 1452-1461, vol. 31, No. 6, Publisher: American Association of Physicists in Medicine.

(Continued)

*Primary Examiner* — John Lacyk
(74) *Attorney, Agent, or Firm* — Eugene J. Molinelli; Beusse Wolter Sanks & Maire

(57) ABSTRACT

A method and apparatus for irradiation therapy using voxel based function measurements of organs-at-risk (OAR). The method includes determining size and location of each voxel of a plurality of voxels in a reference frame of a radiation device. The method further includes obtaining measurements that relate to utility of tissue type at each voxel. The method further includes determining a subset of the voxels that enclose an organ-at-risk (OAR) volume. The method further includes determining a value of a utility measure $f_j$ at each voxel of the subset based on a corresponding value (Continued)

of the measurements. The method further includes determining a series of beam shapes and intensities which minimize a value of an objective function that is based on a computed dose delivered to an OAR voxel multiplied by the utility measure $f_j$ for that voxel summed over all voxels.

16 Claims, 15 Drawing Sheets

(51) Int. Cl.
| | |
|---|---|
| A61B 6/03 | (2006.01) |
| A61B 6/00 | (2006.01) |
| A61B 5/055 | (2006.01) |
| A61B 5/08 | (2006.01) |
| G06F 19/00 | (2018.01) |
| A61B 5/00 | (2006.01) |

(52) U.S. Cl.
CPC ............ *A61B 6/032* (2013.01); *A61B 6/037* (2013.01); *A61B 6/486* (2013.01); *A61B 6/5211* (2013.01); *A61B 6/5235* (2013.01); *G06F 19/321* (2013.01); *A61B 5/7278* (2013.01); *A61N 5/1081* (2013.01)

(58) Field of Classification Search
USPC ........................................................ 600/1–8
See application file for complete search history.

(56) References Cited

U.S. PATENT DOCUMENTS

| | | |
|---|---|---|
| 2011/0286652 A1 | 11/2011 | Kabus et al. |
| 2013/0303899 A1 | 11/2013 | Mistry et al. |

OTHER PUBLICATIONS

Lu, Y., et al., "Functional dose-volume histograms for functionally heterogeneous normal organs," Phys. Med. Biol., 1997, pp. 345-356, vol. 42, Publisher: IOP Publishing Ltd., Published in: U.K.

Marks, L., et al., "Incorporation of functional status into dose-volume analysis," Medical Physics, Feb. 1999, pp. 196-199, vol. 26, No. 2.

Munley, M, et al., "Bioanatomic IMRT Treatment Planning with Dose Function Histograms," International Journal of Radiation Oncology, Biology, Physics, 2002, pp. 126 vol. 54, No. 2 Supplement.

Wang, D., et al., "Functional dosimetric metrics for predicting radiation-induced lung injury in non-small cell lung cancer patients treated with chemoradiotherapy," Radiation Oncology, 2012, pp. 19, vol. 7, No. 69.

Castillo, R., et al., "Ventilation from four-dimensional computed tomography: density versus Jacobian methods," Physics in Medicine and Biology, 2010, pp. 4661-4685, vol. 55.

Ding, K., et al., "Comparison of Intensity- and Jacobian-Based Estimates of Lung Regional Ventilation," Med. Image Anal., 2008, pp. 752-763, vol. 12.

Fuld, M., et al. "CT-measured regional specific volume change reflects regional ventilation in supine sheep," Journal of Applied Physiology, 2008, pp. 1177-1184, vol. 104.

Guerrero, T., et al, "Quantification of Regional Ventilation from Treatment Planning CT," Int. J. Radiation Oncology Biol. Phys., 2005, pp. 630-634, vol. 62, No. 3, Publisher: Elsevier Inc.

Guerrero, T., et al., "Dynamic ventilation imaging from four-dimensional computed tomography," Physics in Medicine and Biology, 2006, pp. 777-791, vol. 51, Publisher: IOP Publishing Ltd.

Herrmann, P., "Quick Manual Vers. 3.14. build 2," Jul. 2, 2011, pp. 1-11.

Hoffmann, E., et al., "Assessment of the Pulmonary Structure-Function Relationship and Clinical Outcomes Measures: Quantitative Volumeric CT of the Lung," Acad. Radial., 1997, pp. 758-776, vol. 4.

Ibanez, L., et al, "The ITK Software Guide," Aug. 21, 2003, 565 page.

Kabus, S., et al., "Evaluation of 4D-CT Lung Registration," Med. Image Comput. Assist. Interv., 2009, pp. 747-754, Publisher: Springer-Verlag.

Mistry, M. et al., "Evaluation of Fraction Regional Ventilation Using 4D-CT and Effects of Breathing Maneuvers on Ventilation," Int. J. Radiation Oncol. Biol. Phys., 2013, pp. 825-831, vol. 87.

Salomao, S., et al., "Integrating computer-aided diagnosis tools into the picture archiving and communication system," Radial. Bras., 2011, pp. 374-380, vol. 44, No. 6.

Simon, B., "Non-Invasive Imaging of Regional Lung Function Using X-Ray Computer Tomography," Journal of Clinical Monitoring and Computing, 2000, pp. 433-442, vol. 16.

Strickland, N., "PACS (picture archiving and communication systems): filmless radiology," Arch Dic Child, 2000, pp. 82-86, vol. 83.

Yamamoto, T., et al., "Four-dimensional computed tomography pulmonary ventilation images vary with deformable image registration algorithms and metrics," Med. Phys., Mar. 2011, pp. 1348-1358, vol. 38, No. 3.

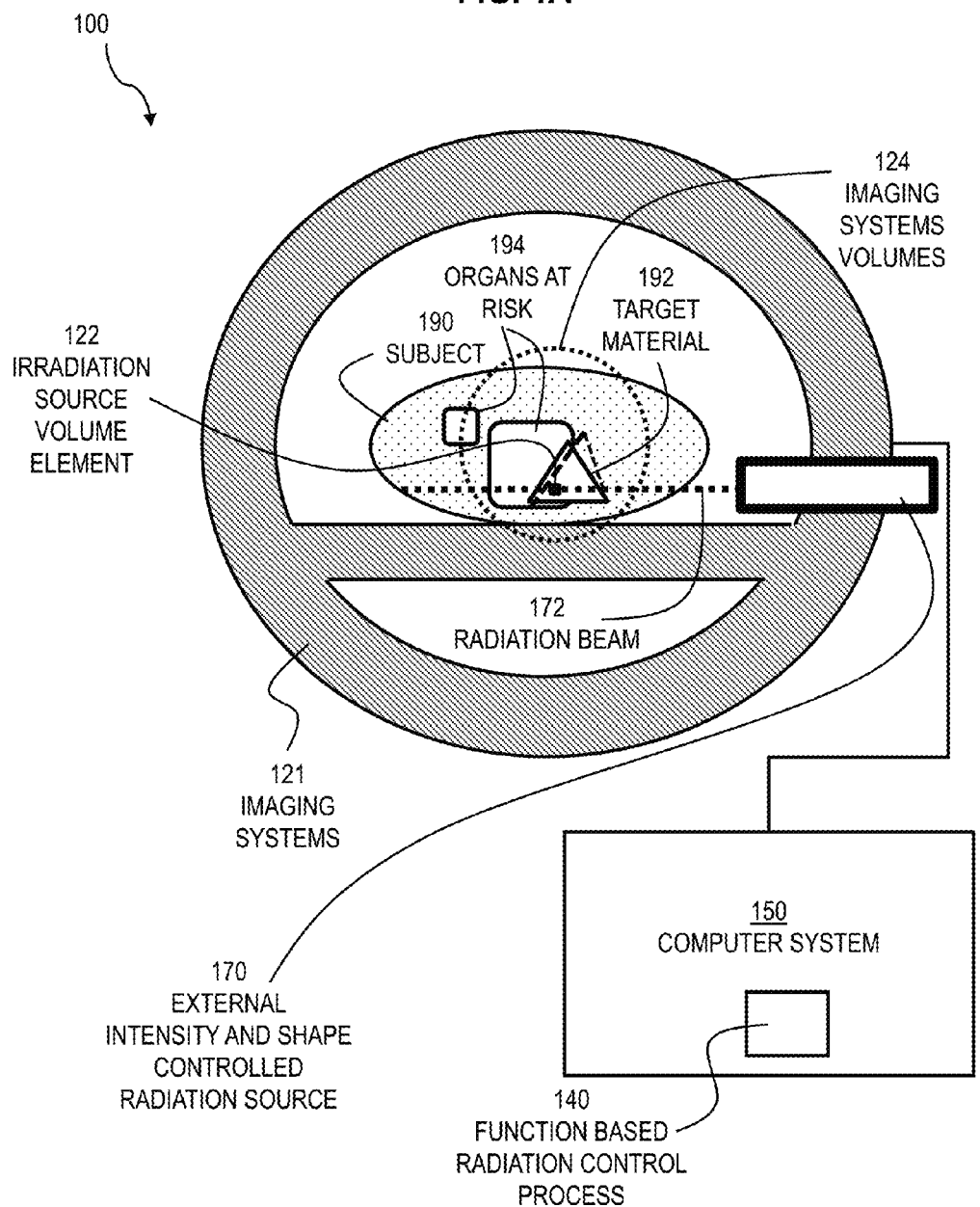

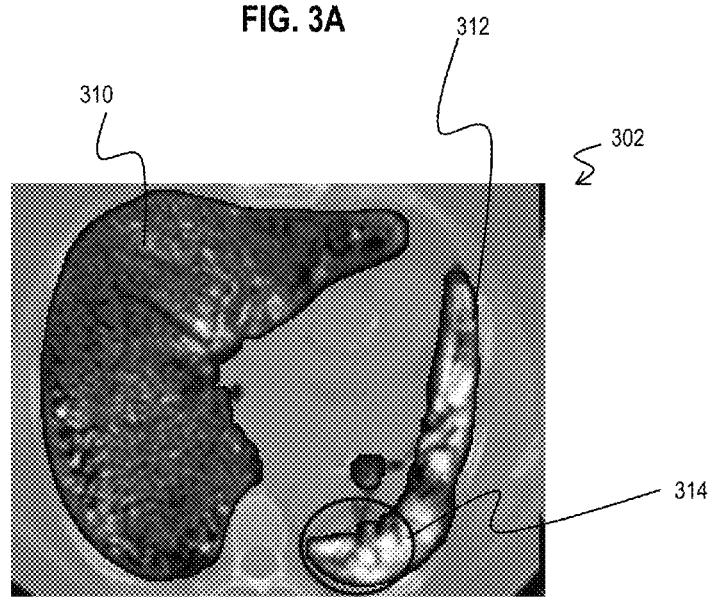
FIG. 3A
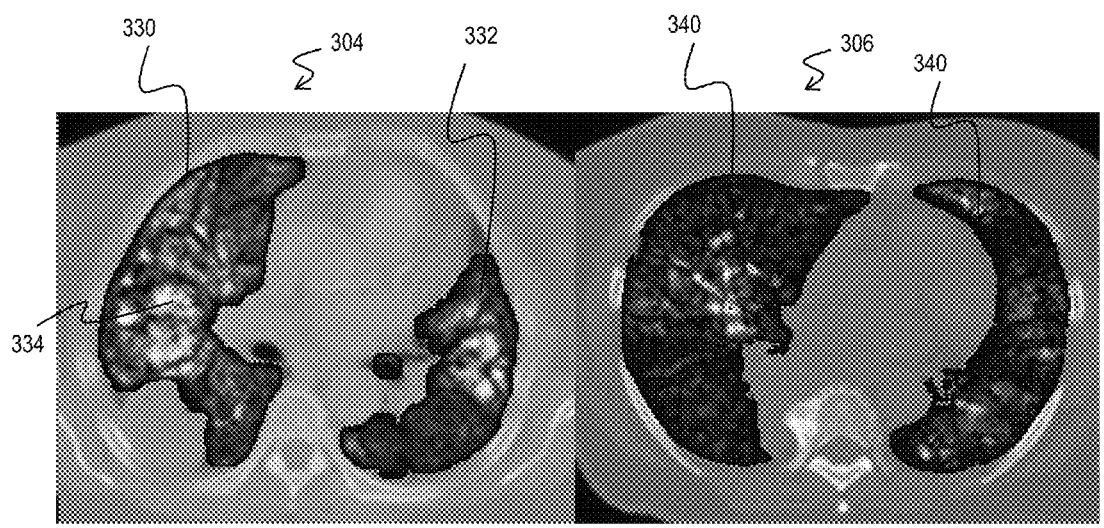
FIG. 3B
FIG. 3C

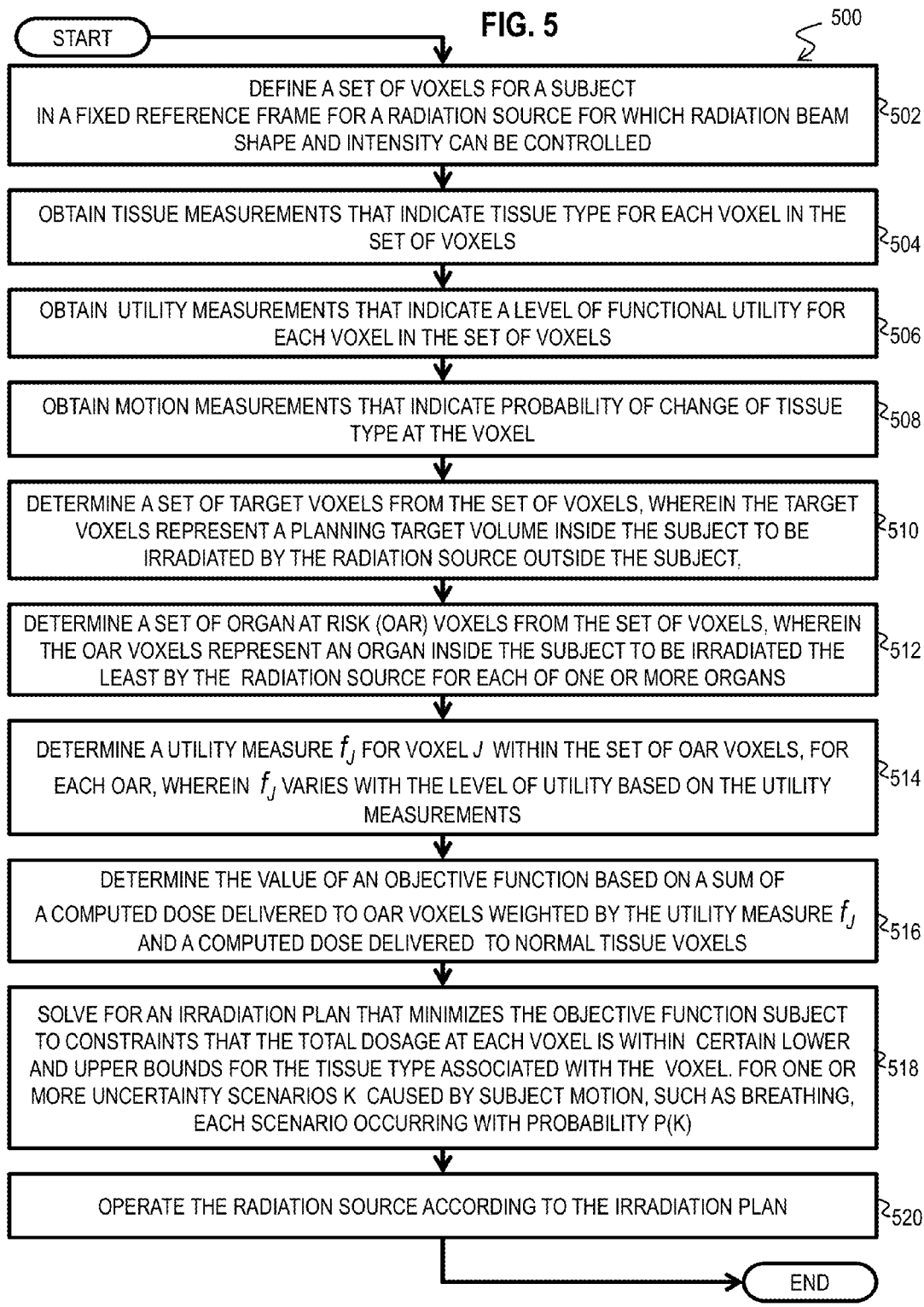

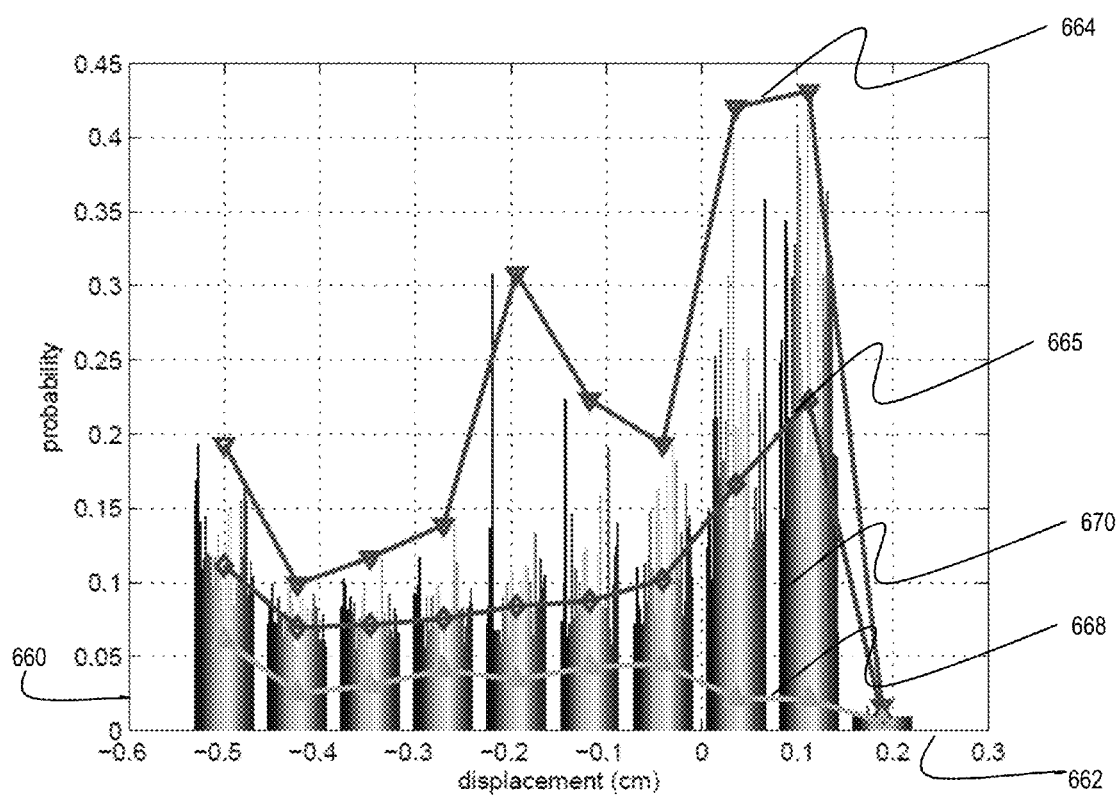

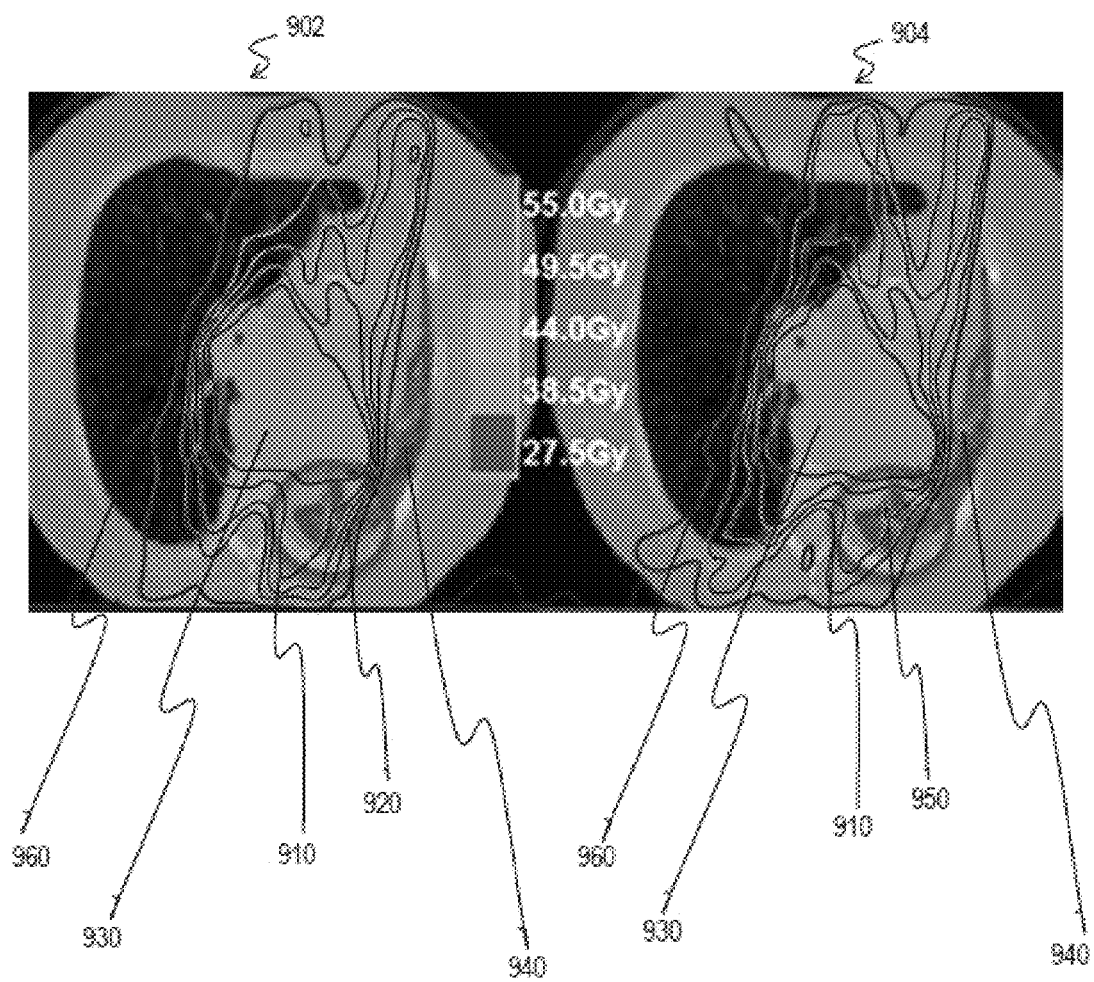

SYSTEM AND METHOD FOR IRRADIATION THERAPY USING VOXEL BASED FUNCTIONAL MEASUREMENTS OF ORGANS AT RISK

CROSS-REFERENCE TO RELATED APPLICATIONS

This application claims benefit of Provisional Appln. 62/029,590, filed Jul. 28, 2014, the entire contents of which are hereby incorporated by reference as if fully set forth herein, under 35 U.S.C. § 119(e).

BACKGROUND

Radiotherapy is a treatment for cancer patients involving the use of high-energy radiation. When high-energy radiation is delivered to a subject, it kills cells in the body. Although the high-energy radiation kills tumor cells in the subject's body, it may also kill normal tissue cells and tissue cells of an organ-at-risk (OAR) that surround the tumor. Thus, the goal of conventional radiotherapy is to deliver a sufficient radiation dose to the tumor to kill the tumor cells while minimizing the radiation dose delivered to the normal tissue cells and OAR tissue cells that surround the tumor.

SUMMARY

It is here recognized that conventional methods for irradiation therapy are deficient, since all volume within the OAR is weighted equally and thus equal sparing is given to all volume within the OAR from the radiation dose. As a result, OAR function heterogeneity is not considered within the volume, which introduces a risk of distributing high radiation doses to OAR regions corresponding to high organ function. This can result in higher normal tissue toxicity or fatal radiation-induced complications.

In a first set of embodiments, a method is provided for irradiation therapy using voxel based functional measurements of organs-at-risk (OAR). The method includes determining size and location of each voxel of a plurality of voxels in a reference frame of a radiation device that emits a beam of radiation with controlled intensity and beam cross sectional shape. The method further includes obtaining, on a processor, first measurements that relate to tissue type inside a subject at each voxel of the plurality of voxels based on a first imaging device. The method further includes obtaining, on a processor, different second measurements that relate to utility of tissue type inside the subject at each voxel of the plurality of voxels based on a second imaging device. The method further includes determining a first subset of the plurality of voxels that enclose a target volume to be irradiated with a therapeutic dose of radiation by the radiation device. The method further includes determining a second subset of the plurality of voxels that enclose an organ-at-risk (OAR) volume. The method further includes determining, on the processor, a value of a utility measure $fj$ at each voxel of the second subset based on a corresponding value of the second measurements. The method further includes determining, on the processor, a series of beam shapes and intensities from the radiation device which minimize a value of an objective function that is based on a computed dose delivered to an OAR voxel multiplied by the utility measure $fj$ for that voxel summed over all voxels. The method further includes controlling the radiation device to deliver the series of beam shapes and intensities.

In a second set of embodiments, a computer-readable medium carrying one or more sequences of instructions is provided, where execution of the one or more sequences of instructions by one or more processors causes the one or more processors to perform the step of receiving first measurements from a first imaging device that relate to tissue type inside a subject at each voxel of a plurality of voxels. Additionally, execution of the one or more sequences of instructions further causes the processor to perform the step of receiving different second measurements from a second imaging device that relate to utility of tissue type inside the subject at each voxel of the plurality of voxels. Additionally, execution of the one or more sequences of instructions further causes the processor to perform the step of determining a value of a utility measure $fj$ at each voxel of a subset of the plurality of voxels that enclose an organ-at-risk (OAR) volume inside the subject based on a corresponding value of the second measurements. Additionally, execution of the one or more sequences of instructions further causes the processor to perform the step of determining a series of beam shapes and intensities from a radiation device which minimize a value of an objective function that is based on a computed dose delivered to an OAR voxel multiplied by the utility measure $fj$ for that voxel summed over all voxels. Additionally, execution of the one or more sequences of instructions further causes the processor to perform the step of controlling the radiation device to deliver the series of beam shapes and intensities.

In a third set of embodiments, a system is provided for irradiation therapy using voxel based functional measurements of organs-at-risk (OAR). The system includes a radiation device to emit a beam of radiation with controlled intensity and beam cross sectional shape in each voxel of a plurality of voxels in a reference frame of the radiation device. The system further includes one or more imaging devices to obtain one or more measurements that relate to tissue type inside a subject at each voxel of the plurality of voxels. The system further includes at least one processor and at least one memory including one or more sequence of instructions. The memory and the sequence of instructions are configured to, with the processor, cause the processor to receive the one or more measurements from the one or more imaging devices; to determine a value of a utility measure $f_j$ at each voxel of a subset of the plurality of voxels that enclose an organ-at-risk (OAR) volume inside the subject based on a corresponding value of the one or more measurements; to determine the controlled intensity and beam cross sectional shape in each voxel that minimize a value of an objective function that is based on a computed dose delivered to an OAR voxel multiplied by the utility measure $f_j$ for that voxel summed over all voxels and to control the radiation device to deliver the series of beam shapes and intensities.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1A is a block diagram that illustrates an example system for irradiation therapy using voxel based functional measurements of organs-at-risk (OAR), according to an embodiment;

FIG. 3A is an image that illustrates an example scanned image to identify example utility of a tissue type in a first subject, where an example area of high utility has been identified, according to an embodiment;

FIG. 3B is an image that illustrates an example scanned image to identify example utility of a tissue type in a second subject, according to an embodiment;

FIG. 3C is an image that illustrates an example scanned image to identify example utility of a tissue type in a third subject, according to an embodiment;

FIG. 5 is a flow diagram that illustrates an example of a method for irradiation therapy using voxel based functional measurements of organs-at-risk (OAR), according to an embodiment;

FIG. 6C is a graph that illustrates an example of curves that provide respective low probability, average probability and high probability that the OAR will remain within a range of the nominal position, over multiple movement phases, according to an embodiment;

FIG. 9A is an image that illustrates the example scanned image of FIG. 2C and identifies multiple example contour lines of radiation dose levels based on a conventional radiotherapy plan;

FIG. 9B is an image that illustrates the example scanned image of FIG. 2B and identifies example contour lines of radiation dose levels, according to an embodiment;

DETAILED DESCRIPTION

Figure 1B:
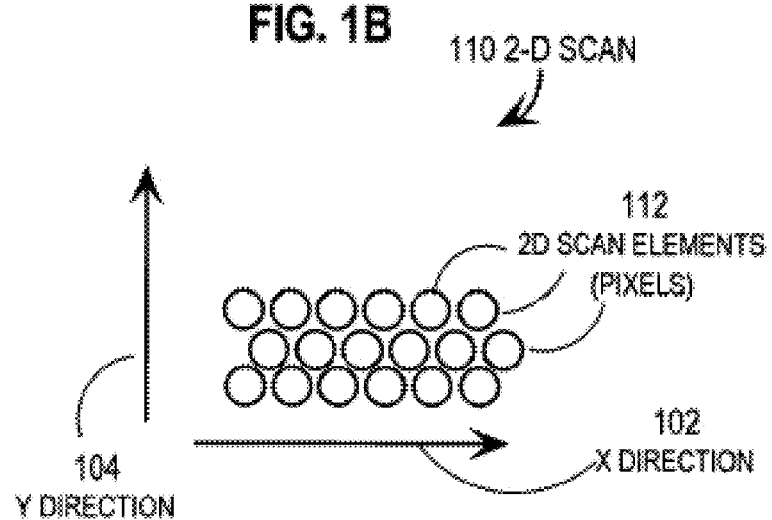
FIG. 1B is a block diagram that illustrates scan elements in a 2D scan, such as one scanned image from a CT scanner.

A method and apparatus are described for irradiation therapy using voxel based functional measurements of organs-at-risk (OAR). In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of irradiation therapy for a mass in or near an OAR, such as a lung. However, the invention is not limited to this context. In other embodiments other target materials and organs are involved as the OAR. For example, target tumor metabolism and hypoxia are applicable to the invention. Additionally, in other examples, other OARs such as the brain, liver, kidney and neck are applicable to the invention.

1. Overview

FIG. 1A is a block diagram that illustrates an example system 100 for irradiation therapy using voxel based functional measurements of organs-at-risk (OAR), according to an embodiment. For purposes of illustration, a living subject 190 is depicted, but is not part of the system 100. One or more imaging systems 121 are provided, to scan images of the subject 190 within an imaging systems volume 124 that encompasses part of the subject 190. In an example embodiment, the volume 124 may encompass the entire subject 190. The imaging systems 121 are non-invasive and obtain cross-sectional images that are axially stacked to generate imaging data of the volume 124. In an example embodiment, the imaging system 121 is a first imaging device that obtains first measurements that relate to tissue type inside the volume 124. For example, the first imaging device is an X-ray Computed tomography (CT) scanner or a nuclear magnetic resonance imagery (MRI) scanner. In an example embodiment, the imaging system 121 includes a second imaging device that obtains second measurements that relate to utility of tissue type inside the volume 124. For example, the second imaging device is a positron emission tomography (PET) scanner, a Single photon emission computed tomography (SPECT) scanner, a functional magnetic resonance imager (fMRI) or a four-dimensional computed tomography (4DCT)-based ventilation/perfusion imaging system. The imaging systems 121 can be operated at different times, to generate different measurements of the tissue type inside the volume 124.

As illustrated in FIG. 1A, a target material 192 indicated by a triangle is positioned within the subject 190. In an example embodiment, the target material 192 includes tumor cells. During movement phases of the subject 190, such as during a breathing phase or heartbeats, the target material 192 shifts from a nominal position to a secondary position indicated by the triangle with the broken line. Thus, at any given instance in time, the actual position of the target material 192 may not be the nominal position. FIG. 1A depicts the movement of target material 192 between the nominal position (solid line) and secondary position (dashed line). Additionally, a pair of OARs 194 is positioned within the subject 190. The region of the volume 124 that is not occupied by the target material 192 or the OAR 194 is occupied by tissues in a category called normal tissue.

As illustrated in FIG. 1A, the system 100 includes a radiation source 170 that emits a beam 172 that penetrates the volume 124 over a plurality of volume elements or voxels 122 that are defined within a frame of reference of the radiation source 170. The radiation source 170 transmits the beam 172 to each voxel 122 along the beam with an intensity and shape that is dependent on how many of each voxel 122 along the beam is occupied by the target material 192, the OAR 194 or normal tissue. Combining the effects of multiple beams (their intensities and shapes), the goal is to transmit high dose to the target material 192, and low dose to the normal tissue and the OAR 194. A probability function is used to account for the movement phases of the subject 190, and whether the classification of the target material 192, the OAR 194 or normal tissue for each voxel 122 along the beam will change at various movement phases of the subject 190.

During the operation of the system 100, the radiation source 170 rotates around the subject 190, so that the beam 172 is directed at the target material 192 from multiple directions. At some angular positions of the radiation source 170, the beam 172 needs to pass through the OAR 194 to get to the target material 192. As illustrated in FIG. 1A, when the radiation source 170 rotates to a left side of the target material 192, the beam 172 needs to pass through the OAR 194 to get to the target material 192. However, at other angular positions of the radiation source 170, the beam 172 need not pass through the OAR 194 to get to the target material 192. As illustrated in FIG. 1A, when the radiation source 170 rotates to a top side of the target material 192, the beam 172 need not pass through the OAR 194 to get to the target material 192.

Figure 12:
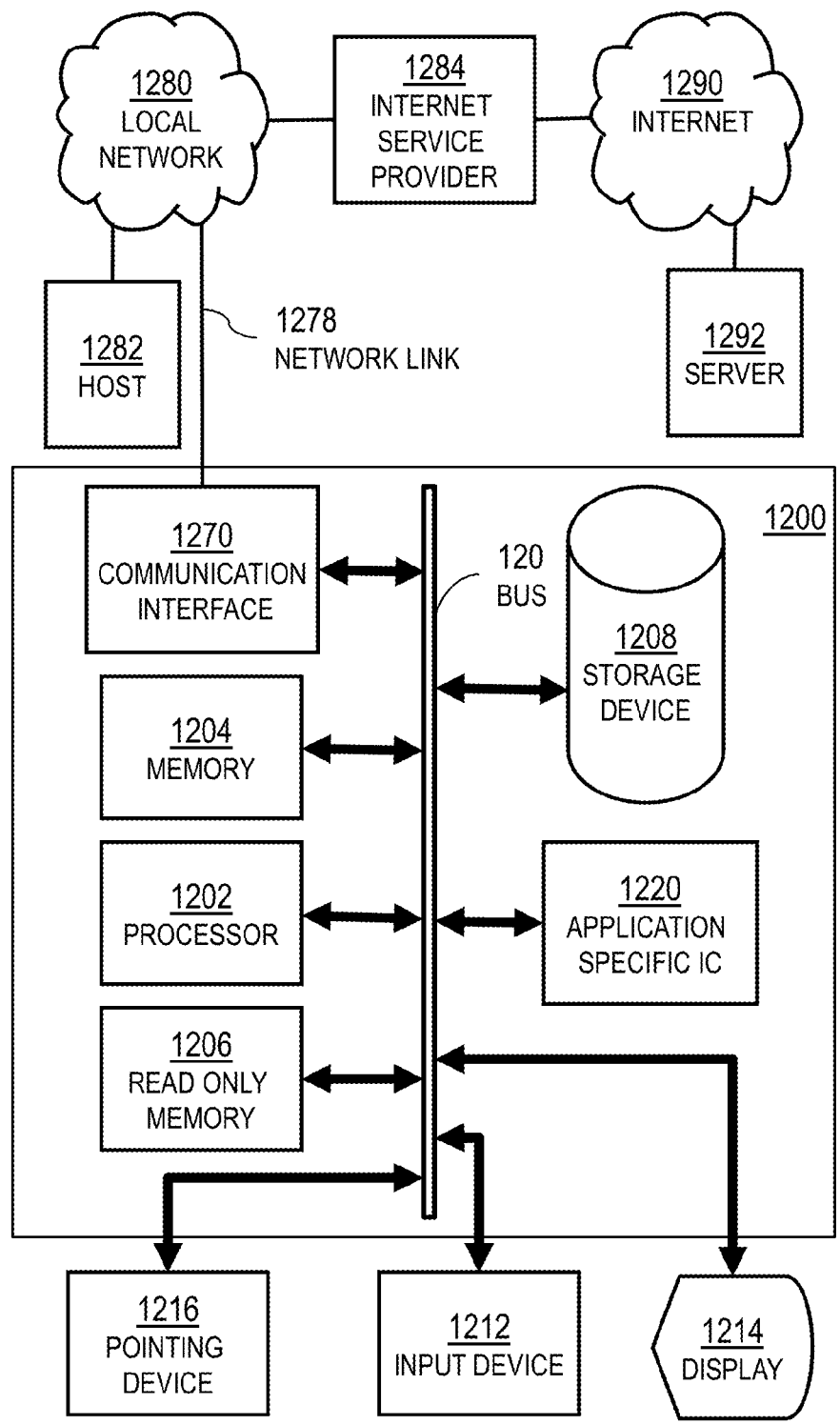
FIG. 12 is a block diagram that illustrates a computer system upon which an embodiment of the invention may be implemented.
Figure 13:
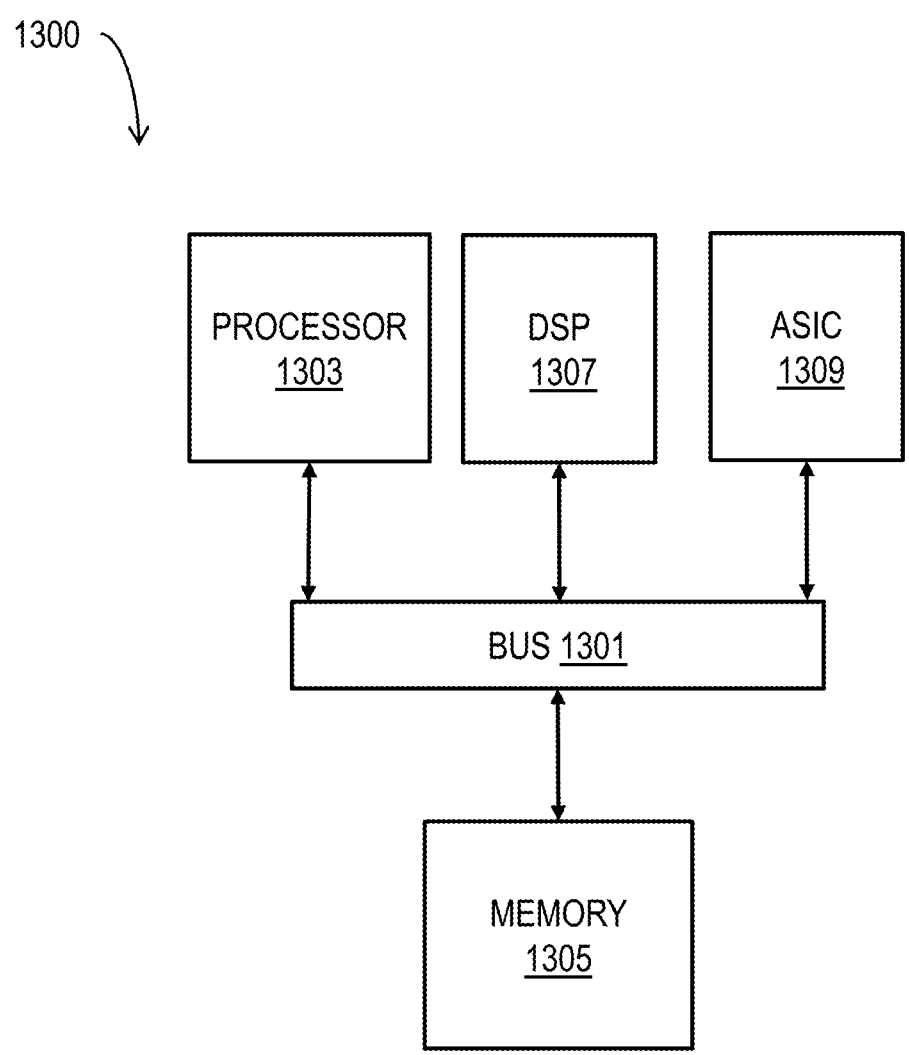
FIG. 13 is a block diagram that illustrates a chip set upon which an embodiment of the invention may be implemented.

As illustrated in FIG. 1A, a computer system 150 is provided to control the one or more imaging systems 121, to collect imaging data from the one or more imaging systems 121, to determine the intensity and shape of the beam 172 delivered to each voxel 122 in the volume 124 and to transmit the intensity and shape of the beam 172 for multiple beams to the radiation source 170. The computer system 150 includes a function based radiation control process 140 to perform one or more steps of a method described below with reference to FIG. 5. In various embodiments, the computer system 150 comprises one or more general purpose computer systems, as depicted in FIG. 12 or one or more chip sets as depicted in FIG. 13, and instructions to cause the computer or chip set to perform one or more steps of a method described below with reference to FIG. 5.

FIG. 1B is a block diagram that illustrates scan elements in a 2D scan 110, such as one scanned image of the volume 124 from the imaging system 121, such as a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement of the living body. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI. Although a particular number and arrangement of equal sized circular scan elements 112 are shown for purposes of illustration, in other embodiments, more elements in the same or different arrangement with the same or different sizes and shapes are included in a 2D scan.

Figure 1C:
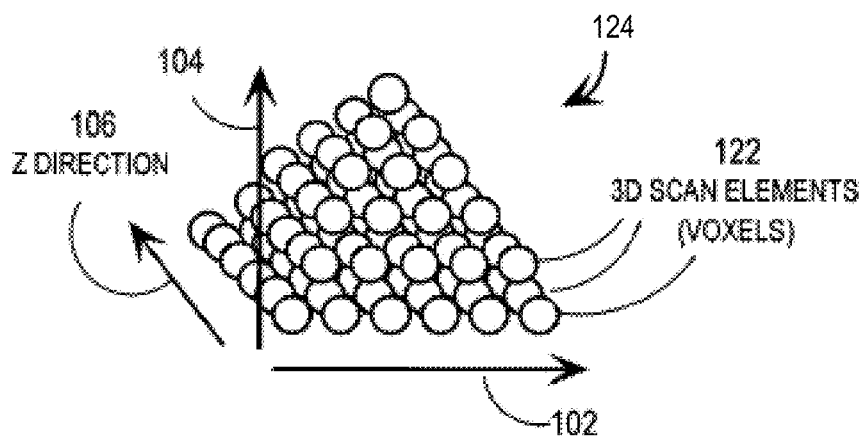
FIG. 1C is a block diagram that illustrates a plurality of voxels within a fixed frame of reference of the radiation source of FIG. 1A.

FIG. 1C is a block diagram that illustrates the plurality of voxels 122 that are defined in the volume 124 within a fixed frame of reference of the radiation source 170 of FIG. 1A. The fixed frame of reference of the radiation source 170 is defined based on the x-direction 102, y-direction 104 and z-direction 106. Thus, in an example embodiment, a particular voxel 122 within the volume 124 in the frame of reference of the radiation source 170 is assigned a unique x-value, y-value and z-value. As previously discussed, some of the voxels 122 are occupied by target material 192, some of the voxels 122 are occupied by OAR material 194 and the remaining voxels 122 in the volume 124 are occupied by normal tissue. The computer system 150 determines the respective intensity and shape of the beam 172. Although a particular number and arrangement of equal voxel 122 are shown for purposes of illustration, in other embodiments, more voxels 122 in the same or different arrangement with the same or different sizes and shapes are included in the frame of reference of the radiation source 170. In an example embodiment, the voxel 122 has a length in a range of 3-5 millimeters, a width in a range of 3-5 millimeters and a depth in a range of 2-3 millimeters.

Figure 2A:
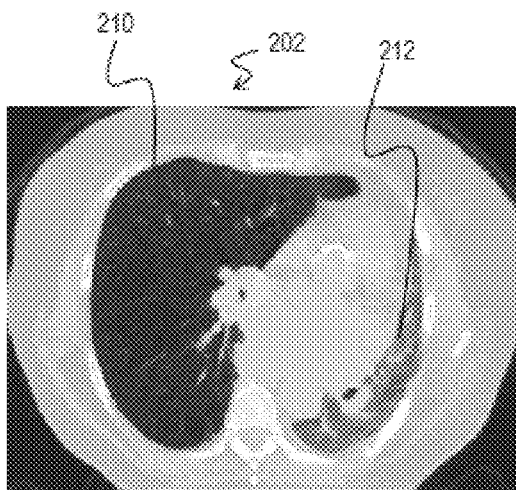
FIG. 2A is an image that illustrates an example of a scanned image to identify tissue type in a subject, such as a scanned image from a CT scanner, according to an embodiment.
Figure 2B:
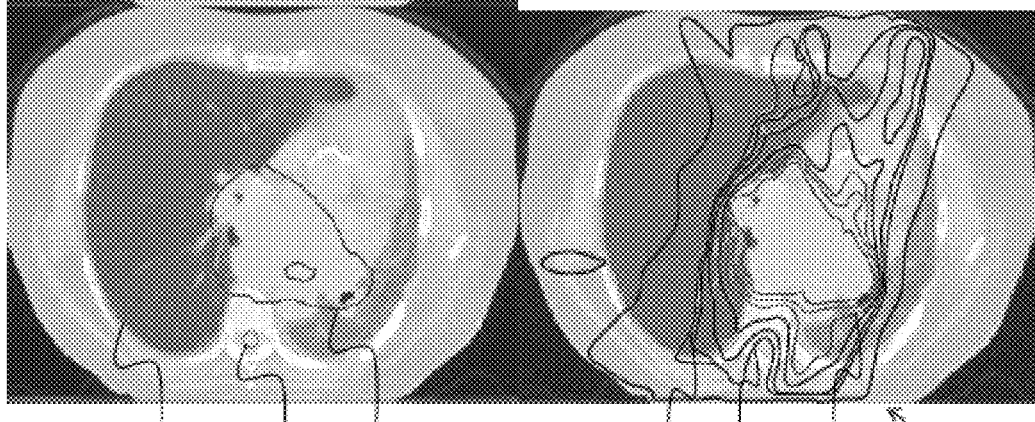
FIG. 2B is an image that illustrates the example scanned image of FIG. 2A, where an example target area and OAR have been identified, according to an embodiment.

FIG. 2A is a block diagram that illustrates a scanned image 202 to identify tissue type in the subject 190 from one of the imaging systems 121, such as a CT scanner. As illustrated in the scanned image 202, a left lung 210 and right lung 212 tissue types (dark) can be identified and differentiated from non-lung tissue types (light gray and white) in the image 202. FIG. 2B is a block diagram that illustrates a scanned image 204 to identify tissue type in the subject 190 that is similar to the scanned image 202, where a target area 218 and a spinal cord 216 (OAR) have been identified. In an example embodiment, an oncologist marked the target area 218 of a tumor and the spinal cord 216, during the development of a conventional radiotherapy treatment plan. During conventional radiotherapy, a treatment plan is developed, which maximizes the radiation dose delivered to the target area 218, while minimizing the radiation dose delivered to the OARs including the lungs 210, 212 and spinal cord 216.

Figure 2C:
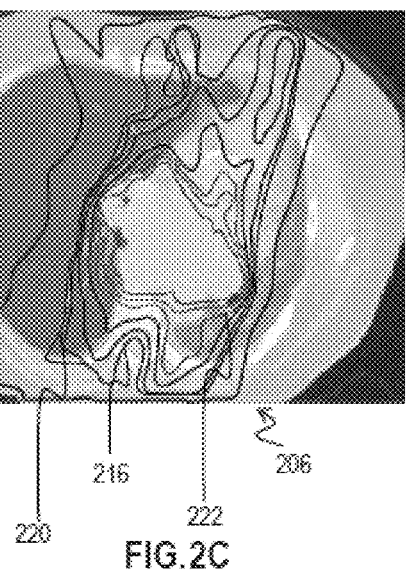
FIG. 2C is an image that illustrates the scanned image of FIG. 2A, with example contour lines of radiation dose levels, based on a conventional radiotherapy plan.

FIG. 2C is a block diagram that illustrates a scanned image 206 to identify tissue type in the subject 190 that is similar to the scanned image 204 and includes contour lines 222 of radiation dose levels, based on the conventional radiotherapy plan. As illustrated in FIG. 2C, contour lines 222 of high radiation dose encircle the target area 218, indicating that the target area 218 receives a high radiation dose, to kill the tumor cells in the target area 218. Additionally, as illustrated in FIG. 2C, contour lines 220 of decreasing radiation dose are provided at increasing distance from the target area 218, to spare the OARs including the lungs 210, 212 and spinal cord 216 from high radiation doses. As illustrated in FIG. 2C, the high radiation dose contour lines are shaped to avoid the OAR (spinal cord 216), in order to spare the OAR from high radiation. During the computation of the treatment plan for conventional radiotherapy, all OAR voxels are given the same weight, when minimizing the radiation dose delivered to the OAR. As further illustrated in FIG. 2C, in computing the treatment plan, at least part of the lung 210 is exposed to a radiation dose, as indicated by contour line 220, in order to cover all of the target area 218 with a sufficient high radiation dose to kill the tumor cells.

FIG. 3A is a block diagram that illustrates a scanned image 302 to identify utility of an OAR such as lungs 310, 312 in a first subject, where an area 314 of high utility has been identified. In an example embodiment, the scanned image 302 is generated with the imaging system 121, such as a positron emission tomography (PET) scanner, a Single photon emission computed tomography (SPECT) scanner, a functional magnetic resonance imager (fMRI) or a four-dimensional computed tomography (4DCT)-based ventilation/perfusion imaging system. The image 302 uses a gray scale, where white indicates a high utility area of the lungs 310, 312 and black indicates a low utility area of the lungs 310, 312. During the development of a treatment plan for radiotherapy, it would be advantageous to ensure that a lower radiation dose is delivered to high utility areas of the OAR, including the area 314 depicted in FIG. 3A.

FIG. 3B is a block diagram that illustrates a scanned image 304 to identify utility of an OAR such as lungs 330, 332 in a second subject. FIG. 3C is a block diagram that illustrates a scanned image 306 to identify utility of an OAR such as lungs 340, 342 in a third subject. By comparing FIG. 3A-FIG. 3C, it is apparent that the utility of the lungs between the subjects varies considerably. For example, the area 314 of high utility in the right lung 312 of the first subject (FIG. 3A) is not an area of high utility in the right lung 332 of the second subject (FIG. 3B). In another example, an area 334 of high utility in the left lung 330 of the second subject (FIG. 3B) is not an area of high utility in the left lung 310 of the first subject (FIG. 3A). During the development of a treatment plan for radiotherapy, it would be further advantageous to consider the individualized utility of the OARs of each subject, so that the treatment plan is tailored for each subject.

Figure 4:
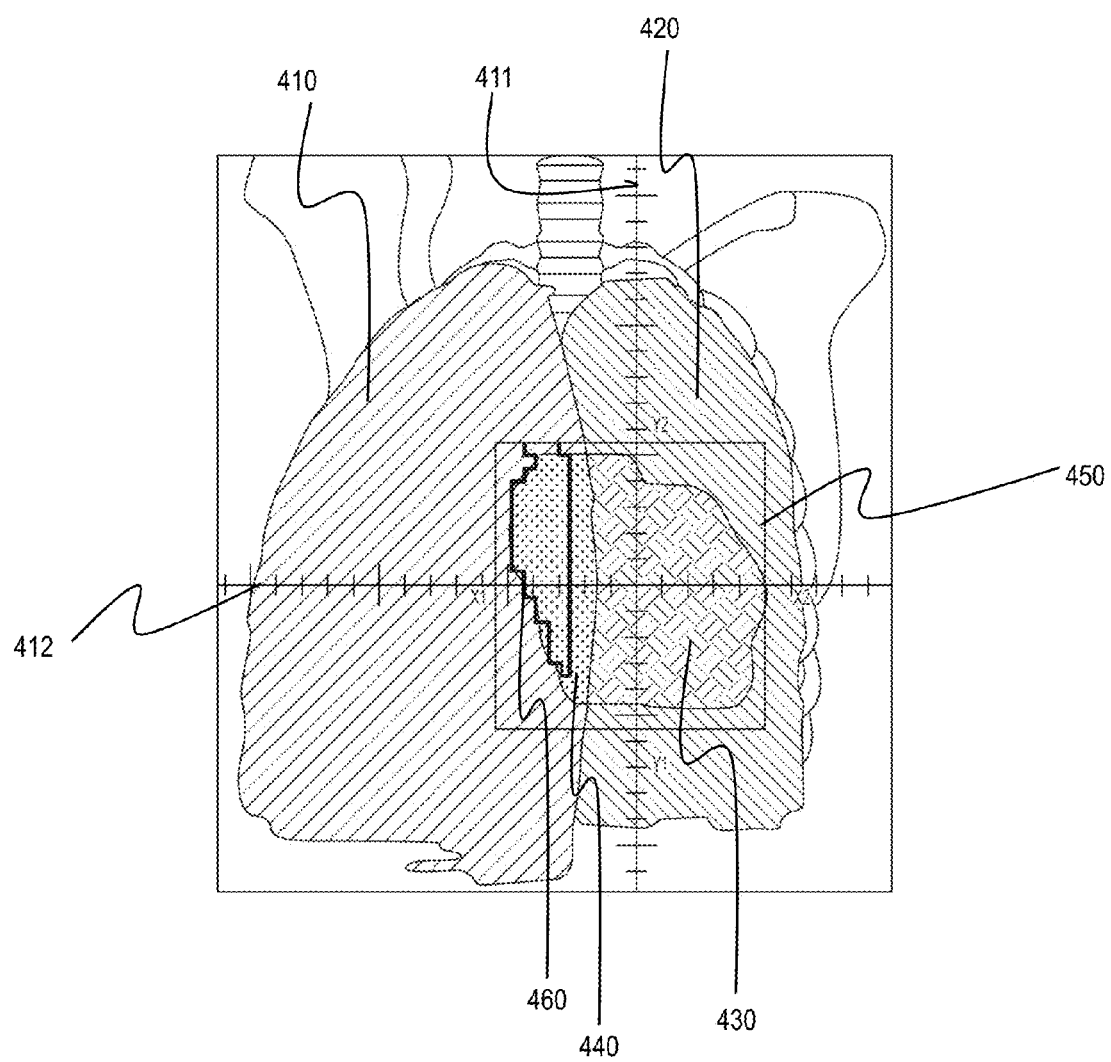
FIG. 4 is a block diagram that illustrates an example OAR and example target material in an example frame of reference of the example radiation source of FIG. 1A, according to an embodiment.

FIG. 4 is a block diagram that illustrates a shape of a beam, an OAR such as lungs 410, 420 and target material 430, 440 in a frame of reference of the radiation source 170 of FIG. 1A, according to an embodiment. The frame of reference of the radiation source 170 includes an x-dimension 412 and a y-dimension 411. The radiation source 170 can irradiate a range 450 within the frame of reference, defined between $x_1$ and $x_2$ in the x-dimension 412 and $y_1$ and $y_2$ in the y-dimension 411. A plurality of rectangles (not shown) or multi-leaf collimators are positioned in a head of the radiation source 170 and are selectively positioned to shape the beam 172 in one of a plurality of directions at a selective portion of the range 450 for one of multiple time intervals. As depicted in FIG. 4, the beam 172 is shaped at a portion 460 of the target material 440 in one of a plurality of directions for one of multiple time intervals. After the radiation source 170 is arranged so that the beam 172 is shaped in one direction as depicted in FIG. 4, the radiation source 170 may transmit the beam 172 at selective intensities for selective time intervals, before the radiation source 170 is reconfigured to shape the beam 172 in another direction to the target material 430, 440.

As further illustrated in FIG. 4, a first portion of the target material 430 is on a near side of the radiation source 170 and thus the beam 172 passes into the first portion of the target material 430 without passing into the lung 410, and before passing into the lung 420 of the subject. However, a second portion of the target material 440 is positioned on a far side of the left lung 410 and thus the beam 172 needs to pass through the left lung 410 in order to reach the second portion of the target material 440. Thus, when developing the treatment plan for radiotherapy, in order to ensure that the target material 430, 440 receives a sufficient amount of high radiation dose to kill all tumor cells in the target material 430, 440, the lung 410 will necessarily receive some dose of radiation. It would be advantageous to ensure that the portions of the lung 410 which receive this dose of radiation are not high utility areas such as area 314 in FIG. 3A, in order to preserve these high utility areas of the OAR. When the beam 172 is oriented at the target material 430, 440 at a different direction than the direction depicted in FIG. 4, the beam 172 may pass into the second portion of the target material 440 without needing to pass through the lung 410.

FIG. 5 is a flow diagram that illustrates an example of a method 500 for irradiation therapy using voxel based functional measurements of organs-at-risk (OAR), according to an embodiment. For example, one or more of the steps of method 500 are applied by process 140 of computer system 150. Although the flow diagram of FIG. 5 is depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

After starting, in step 502, the plurality of voxels 122 are defined for the subject 190 in the fixed reference frame for the radiation source 170 for which the radiation beam 172 shape and intensity can be controlled. As depicted in FIG. 1C, the voxels 122 are defined by the three-dimensional axes 102, 104, 106 in the fixed reference frame of the radiation source 170. Additionally, the voxels 122 are positioned within the imaging systems volume 124 that encompasses a portion of the subject 190, such that each voxel 122 is a respective volume element within the volume 124. Additionally, as previously discussed, the intensity and shape of the beam 172 can be controlled by the computer system 150.

In step 504, tissue type measurements are obtained that indicate tissue type for each voxel 122 in the volume 124. In an example embodiment, the imaging system 121 is a first imaging device that obtains the tissue measurements that relate to tissue type inside the volume 124. For example, the first imaging device is an X-ray Computed tomography (CT) scanner or a nuclear magnetic resonance imagery (MRI) scanner. The obtained tissue measurements in step 504 are similar to the scanned image 202 of FIG. 2A which indicate the target 218 tissue type as well as different OAR tissue types, including lung 210, 212 tissue type and spinal cord 216 tissue type. In an example embodiment, the imaging system 121 obtains cross-sectional tissue type measurements that are axially stacked and processed (including registration, interpolation and averaging in various embodiments) to generate imaging of each voxel 122 within the volume 124.

In step 506, utility measurements are obtained that indicate a level of functional utility for each voxel 122 in the volume 124. In an example embodiment, the imaging system 121 is a second imaging device that is the same as or different from the first imaging device and that obtains measurements that relate to utility of tissue type inside the volume 124. For example, the second imaging device is a positron emission tomography (PET) scanner, a Single photon emission computed tomography (SPECT) scanner, a functional magnetic resonance imager (fMRI) or a four-dimensional computed tomography (4DCT)-based ventilation imaging system. The obtained utility measurements in step 506 are similar to the scanned images 302, 304, 306 of FIGS. 3A-3C which indicate the level of functional utility the OAR in each subject. In an example embodiment, the imaging system 121 obtains cross-sectional utility measurements that are axially stacked and processed (including registration, interpolation and averaging in various embodiments) to generate imaging of each voxel 122 within the volume 124.

Imaging systems 121 are currently available to obtain ventilation utility measurements from the lungs. For example, ventilation utility measurements can be obtained of the lungs using 4DCT, as described in Mistry et al. Int J Radiat Oncol Biol Phys. 2013 87(4):825-31, which is incorporated by reference herein. Ventilation utility measurement can also be obtained of the lungs using MRI, as described in Deninger et al. Magn. Reson. Med. 2002 48(2): 223-32, which is incorporated by reference herein. Additionally, ventilation utility measurements can also be obtained of the lungs using SPECT, as described in Suga, Ann. Nucl. Med. 2002 16(5): 303-10, which is incorporated by reference herein.

Imaging systems 121 are currently available to obtain perfusion utility measurements for each OAR. For example, perfusion utility measurements can be obtained of the OAR using CT, as described in Miles et al. Lancet. 1991 337 (8742): 643-5, which is incorporated by reference herein. Perfusion utility measurement can also be obtained of the OAR using SPECT, as described in Catafau, J Nucl. Med. 2001 42(2): 259-71, which is incorporated by reference herein. Additionally, perfusion utility measurements can also be obtained of the OAR using MRI, as described in Berthezene et al. Radiology 1992 183: 667-72, which is incorporated by reference herein.

Imaging systems 121 are currently available to obtain neural utility measurements for the OAR. For example, neural utility measurements can be obtained of each OAR using fMRI, as described in Heeger and Ress, Nature Reviews Neuroscience 2002 3: 142-51, which is incorporated by reference herein. Imaging systems 121 are currently available to obtain utility measurements of tissue elasticity, stress and strain for the OAR. These utility measurements can be obtained of the OAR using Ultrasound, as described in Ophir et al. J Med. Ultrasonics 2002 29: 155-71, which is incorporated by reference herein. Additionally, these utility measurements can also be obtained of the OAR using MRI, as described in Fowlkes et al. Med. Phys. 1995 22: 1771-8, which is incorporated by reference herein.

Imaging systems 121 are currently available to obtain diffusion utility measurements for the OAR. For example, diffusion utility measurements can be obtained of each OAR using MRI, as described in Padhani et al. Neoplasia 2009 11(2): 102-25, which is incorporated by reference herein. Imaging systems 121 are currently available to obtain utility measurements of metabolic signatures for the OAR. These utility measurements can be obtained of the OAR using MRI Spectroscopy, as described in McKnight. Semin. Oncol. 2004 31(5): 605-17, which is incorporated by reference herein.

Figure 6A:
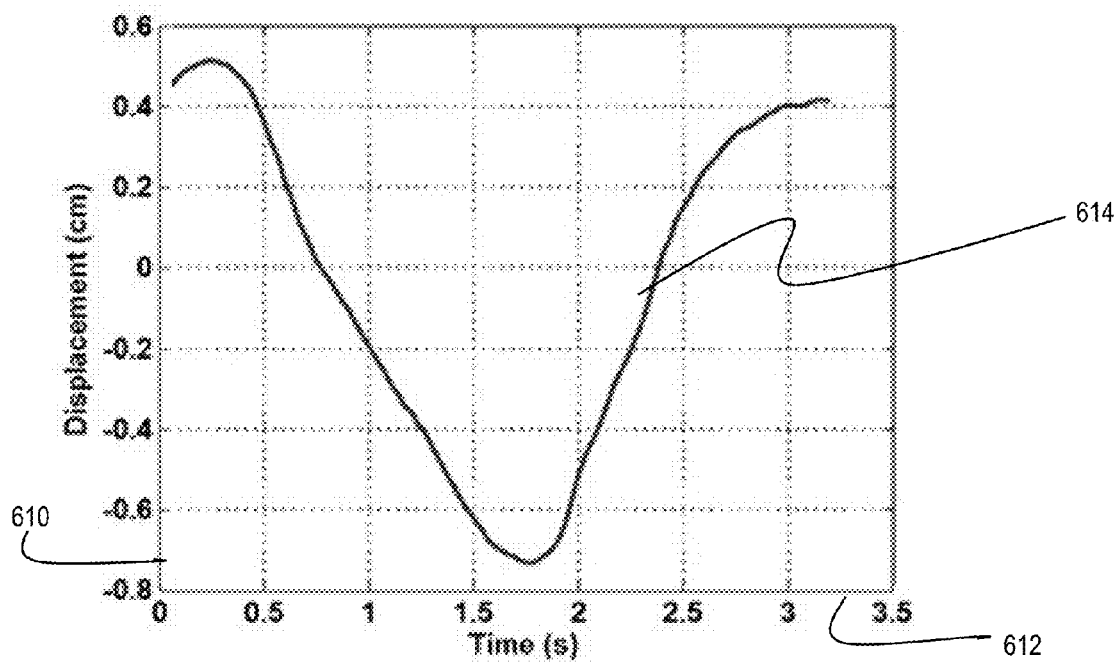
FIG. 6A is a graph that illustrates an example of a displacement of an OAR from a nominal position over a movement phase, according to an embodiment.

In step 508, motion measurements are obtained that indicate a probability of change in tissue type at each voxel 122. As previously discussed, the radiation source 170 transmits the beam 172 aiming to deliver high dose to voxels 122 in the beam that are occupied by the target material 192, transmits the beam 172 to deliver low dose to voxels 122 in the beam that are occupied by the normal tissue and transmits the beam 172 to deliver low dose to voxels 122 in the beam that are occupied by the OAR 194. However, during movement phases of the subject 190, such as during a breathing phase, the tissue classification of each voxel 122 may change. A probability function is used to account for the movement phases of the subject 190, and whether the classification of the target material 192, the OAR 194 or normal tissue for each voxel 122 will change because of various movement phases of the subject 190. FIG. 6A is a graph that illustrates an example of a displacement 614 of an OAR from a nominal position over a movement phase, according to an embodiment. The horizontal axis 612 is time measured in units of seconds (s). The vertical axis 610 is displacement measured in units of centimeters (cm). In an example embodiment, the displacement 614 curve is generated with Varian® real-time position management (RPM).

Figure 6B:
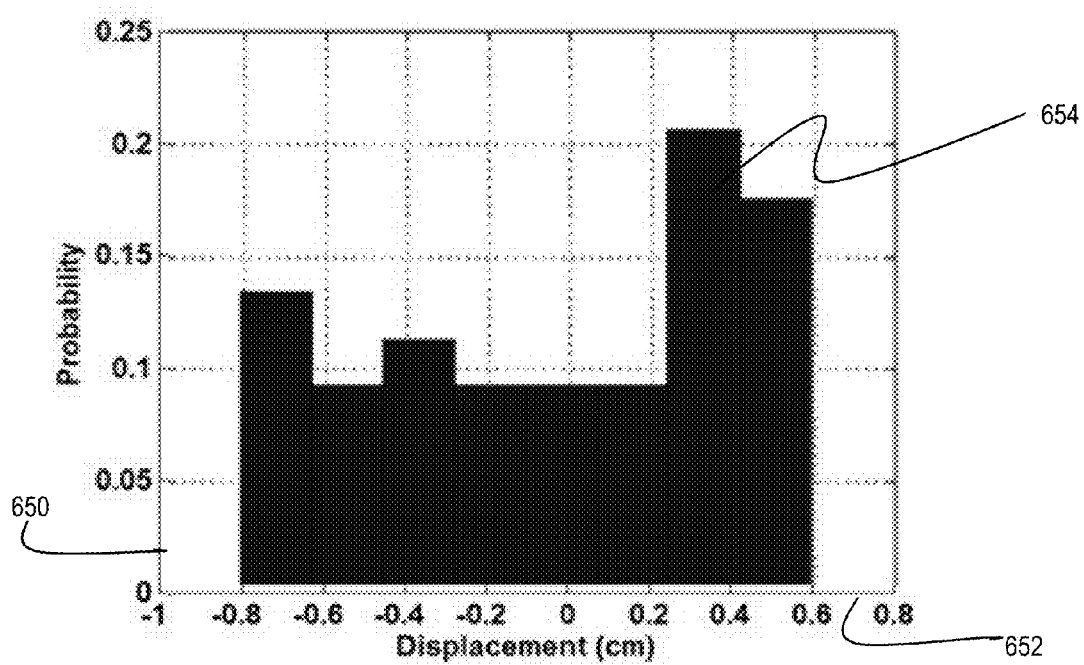
FIG. 6B is a graph that illustrates an example of a probability curve that the OAR will remain within a range of the nominal position, based on the displacement curve of FIG. 6A.

FIG. 6B is a graph that illustrates an example of a probability curve 654 that the OAR will remain within a range of the nominal position, based on the displacement 614 curve of FIG. 6A. The horizontal axis 652 is displacement measured in units of centimeters (cm). The vertical axis 650 is probability measured in a unitless ratio between 0 and 1. For example, if the voxel 122 is centered at the nominal position (0 cm) of the OAR, then the probability curve 654 indicates that the probability that the OAR will move +0.4 cm during the movement phase of the subject 190 is 20%.

As discussed above, the probability curve 654 of FIG. 6B is based on the single displacement 614 curve of the OAR depicted in FIG. 6A. Since each movement phase of the subject 190 is unique, a range of displacement curves of the OAR can be generated based on a range of movement phases of the subject 190. This range of displacement curves can then be used to generate a range of probability curves. FIG. 6C is a graph that illustrates an example of probability curves 670 that provide respective lower bound 668 on the probability, average 665 of the probability and upper bound 664 on the probability that the OAR will remain within a range of the nominal position, over multiple movement phases of the subject 190. The horizontal axis 662 is displacement measured in units of centimeters (cm). The vertical axis 660 is probability measured in a unitless ratio between 0 and 1. In other embodiments, the curves 666, 670 and 664 are used in different ways.

Figure 7:
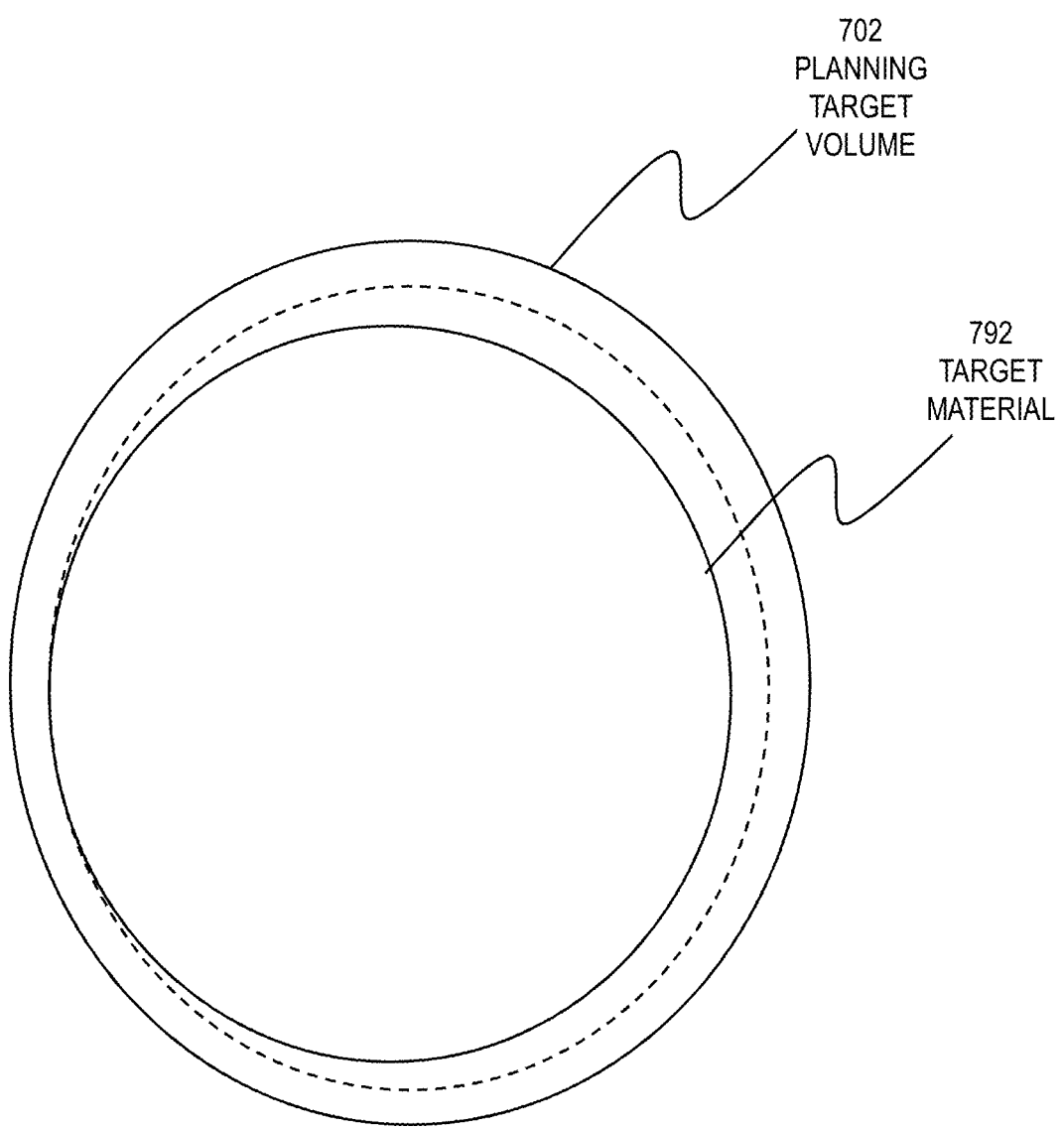
FIG. 7 is a block diagram that illustrates an example of a planning target volume that encloses the target material, according to an embodiment.

In step 510, a set of target voxels are determined from the plurality of voxels 122 within the volume 124. This step is performed, using the tissue type measurements obtained in step 504 that indicate target tissue type in the volume 124. The set of target voxels are determined, to encompass the target material 192 that is positioned within the subject 190. However, the set of target voxels is necessarily expanded beyond the target material 192, to account for the uncertainty of the subject 190. FIG. 7 is a block diagram that illustrates an example of a planning target volume 702 that encloses the target material 792, according to an embodiment. As illustrated in FIG. 7, the planning target volume 702 encompasses the target volume 792 defined by initial imaging (solid line) and in the secondary position (dotted line) resulting from uncertainty. The planning target volume 702 is used to determine the set of target voxels in step 510, to ensure that all of the target material 792 is within the set of target voxels, over all uncertainties. In some embodiments, the uncertainties arise from the movement of the subject 190. In other embodiments, the uncertainties arise from setup of one or more components of the system 100. In an example embodiment, the planning target volume 702 is formed by expanding the target material 192 by a margin in a range of 2 mm-1 cm.

In step 512, a set of OAR voxels are determined from the plurality of voxels 122 within the volume 124. This step is performed, using the tissue type measurements obtained in step 504 that indicate OAR tissue type in the volume 124. The set of OAR voxels are determined, to encompass the one or more OARs 194 within the volume 124. The set of OAR voxels represent the OAR 194 inside the subject 190 to be irradiated the least by the radiation source 170 for each of the one or more OARs 194. Those voxels 122 within the volume 124 that are not determined to be target voxels in step 510 or OAR voxels in step 512 are determined to be normal tissue voxels.

Figure 8A:
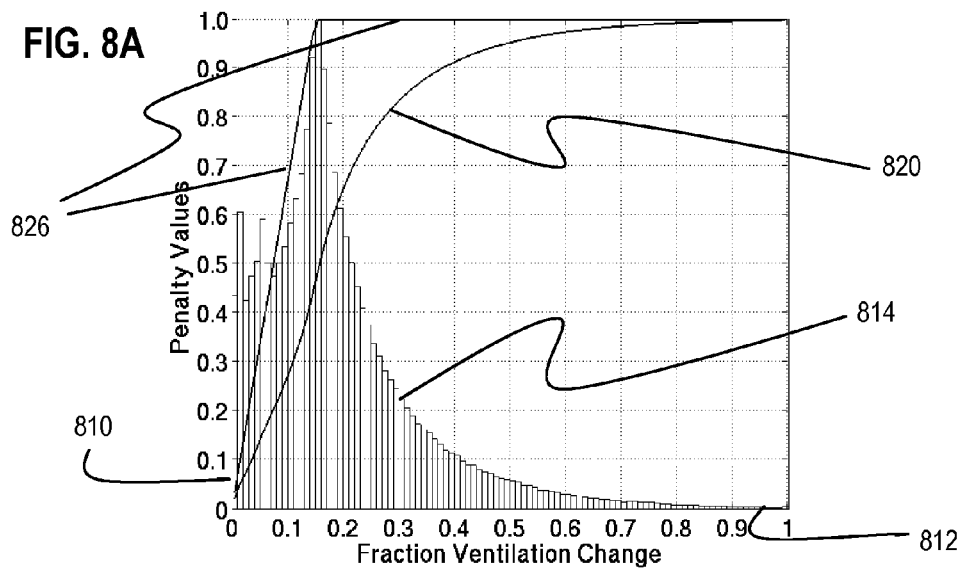
FIG. 8A is a graph that illustrates an example of a histogram of utility measurements at each OAR voxel of the first subject OAR in FIG. 3A and a pair of example curves based on the utility measurements at each OAR voxel, according to an embodiment.
Figure 8B:
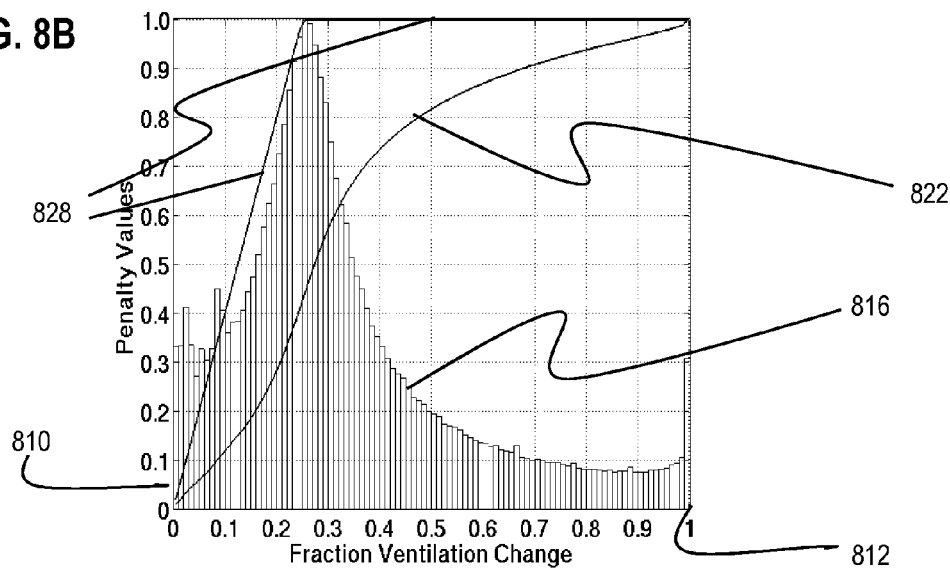
FIG. 8B is a graph that illustrates an example of a histogram of utility measurements at each OAR voxel of the second subject OAR in FIG. 3B and a pair of example curves based on the utility measurements at each OAR voxel, according to an embodiment.
Figure 8C:
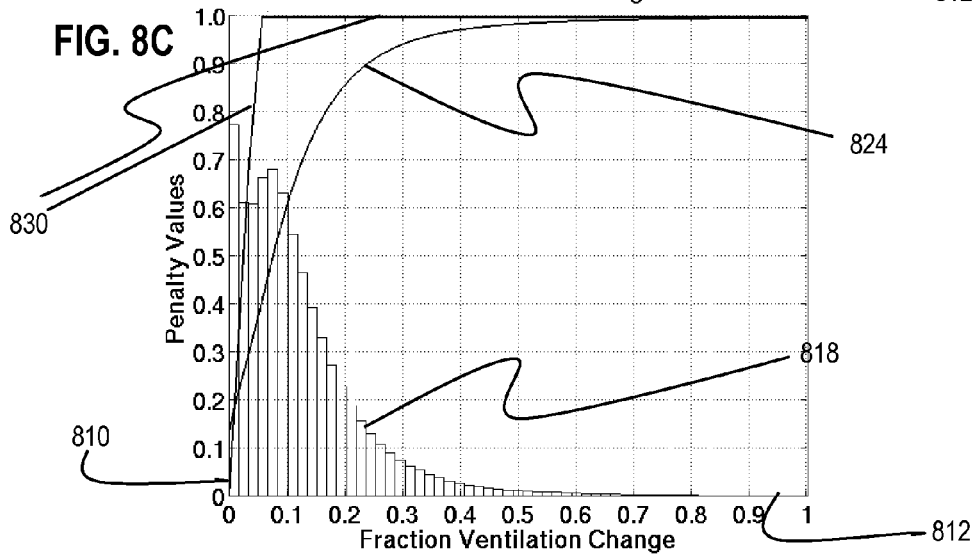
FIG. 8C is a graph that illustrates an example of a histogram of utility measurements at each OAR voxel of the third subject OAR in FIG. 3C and a pair of example curves based on the utility measurements at each OAR voxel, according to an embodiment.

In step 514, a utility measure $f_j$ for each OAR voxel 122 is determined, based on the utility measurements at each OAR voxel obtained in step 506. FIG. 8A is a graph that illustrates an example of a histogram 814 of the utility measurements at each OAR voxel of the scanned image 302 of the first subject in FIG. 3A. The horizontal axis 812 is a unitless ratio between 0 and 1 that indicates the utility measurement of the OAR (as a fraction of ventilation change). In the example embodiment where the OAR are lungs 310, 312 of the first subject, the fraction of ventilation change indicates the ratio of ventilation change of the lung voxel 122 over a breathing phase of the first subject and thus a higher fraction of ventilation change indicates a higher utility measurement. The vertical axis 810 is a normalized quantity of the lung voxels 122 at each utility measurement or fraction of ventilation change. FIG. 8B is a graph that illustrates an example of a histogram 816 of utility measurements at each OAR voxel of the scanned image 304 of the second subject in FIG. 3B. The horizontal axis 812 and vertical axis 810 are similar to those of FIG. 8A. FIG. 8C is a graph that illustrates an example of a histogram 818 of utility measurements at each OAR voxel of the scanned image 306 of the third subject in FIG. 3C. The horizontal axis 812 and vertical axis 810 are similar to those of FIG. 8A.

In an example embodiment, the utility measure $f_j$ for each OAR voxel 122 is determined using a cumulative distribution of the utility measurements. FIG. 8A illustrates a utility measure $f_j$ curve 820 for each OAR voxel 122 that is based on a cumulative distribution of the utility measurements in the histogram 814. The value of the curve 820 at any utility measurement (x) along the horizontal axis 812 is equal to the collective area under the histogram 814 up to that utility measurement (x). FIG. 8B illustrates a utility measure $f_j$ curve 822 for each OAR voxel 122 that is similarly based on a cumulative distribution of the utility measurements in the histogram 816. FIG. 8C illustrates a utility measure $f_j$ curve 824 for each OAR voxel 122 that is similarly based on a cumulative distribution of the utility measurements in the histogram 818. In an example embodiment, the value of the utility measure $f_j$ for each OAR voxel 122 is used to determine a degree of minimization of the radiation dose for each OAR voxel 122. The utility measure $f_j$ curves 820, 822, 824 have increasing values for OAR voxels 122 for higher utility measurements, and thus the minimization of the radiation dose is enhanced for these OAR voxels 122 with higher utility measurement.

In an example embodiment, the utility measure $f_j$ for each OAR voxel 122 is determined using a piecewise linear function of the utility measurements. FIG. 8A illustrates a utility measure $f_j$ piecewise linear function 826 for each OAR voxel 122 including a first line connecting the origin to a peak of the histogram 814 and a second horizontal line equal to the peak value of the histogram 814 for those utility measurements greater than the utility measurement of the peak of the histogram 814. FIG. 8B illustrates a utility measure $f_j$ piecewise linear function 828 for each OAR voxel 122 that is similarly based on a first line connecting the origin to a peak of the histogram 816 and a second horizontal line equal to the peak value of the histogram 816 for those utility measurements greater than the utility measurement of the peak of the histogram 816. FIG. 8C illustrates a utility measure $f_j$ piecewise linear function 830 for each OAR voxel 122 that is similarly based on a first line connecting the origin to a peak of the histogram 818 and a second horizontal line equal to the peak value of the histogram 818 for those utility measurements greater than the utility measurement of the peak of the histogram 818.

In an example embodiment, the value of the utility measure $f_j$ for each OAR voxel 122 is used to determine a degree of minimization of the radiation dose for each OAR voxel 122. Since the utility measure $f_j$ piecewise linear functions 826, 828, 830 have a maximum value at the peak value of the histograms, where a peak number of OAR voxels 122 have a particular utility measurement, the minimization of the radiation is enhanced for this peak number of OAR voxels 122. Additionally, since the utility measure $f_j$ piecewise linear functions 826, 828, 830 has a maximum value for OAR voxels 122 with higher utility measurements, the minimization of the radiation dose is also enhanced for these OAR voxels 122 with higher utility measurement. In other embodiments, $f_j$ is defined based on other functions of the utility measurements. In an example embodiment, the utility measure $f_j$ can be based on any function that has higher values for voxels with higher utility function, so that the dose delivered to those voxels is minimized. For example, the utility measure $f_j$ can be based on any monotonic increasing mathematical function.

In step 516, a value of an objective function is determined based on a sum of a computed radiation dose delivered to OAR voxels 122 weighted by the utility measure $f_j$ at the OAR voxels 122 and a computed dose delivered to normal tissue voxels. The objective function can be expressed as:

$$\alpha^{OAR} \cdot f_j \cdot x_j + \alpha^{NORMAL} \cdot y_j \quad (1)$$

where $\alpha^{OAR}$ and $\alpha^{NORMAL}$ are respective constants for the OAR voxels and the normal tissue voxels. For example, a clinical planner could choose $\alpha^{OAR}=10$ and $\alpha^{NORMAL}=2$ based on their experience to generate radiotherapy plans. If more than one type of OAR is positioned within the volume 124, equation (1) includes a $\alpha^{OAR}$ term for each type of OAR, where the $\alpha^{OAR}$ constant is scaled, depending on the type of OAR. In an example embodiment, if the OAR has a higher priority of sparing, then the $\alpha^{OAR}$ constant has a greater value, to enhance the minimization of the computed dose for that OAR. $f_j$ is the utility measure that was determined in step 514, j is the index of the $j^{th}$ voxel 122 within the volume 124. $x_j$ is the computed dose delivered to the OAR voxels and $y_j$ is the computed dose delivered to the normal tissue voxels. To perform step 516, for each voxel 122 in the volume 124, if the voxel 122 encloses OAR tissue, then the computed dose $x_j$ is multiplied by $f_j$ and the $\alpha^{OAR}$ term. If the voxel 122 encloses normal tissue, then the computed dose $y_j$ is just multiplied by the $\alpha^{NORMAL}$ term. These contributions are then summed for all voxels 122 in the volume 124. As previously discussed in step 514, since the utility measure $f_j$ has an increased value for OAR voxels 122 with a high utility measurement, the computed dose $x_j$ in equation (1) will have a higher priority of minimization for OAR voxels 122 with high utility measurements, as discussed in step 518 below.

In an example embodiment, an objective function can also be defined to include the computed dose delivered to the target tissue voxels within the volume 124, which can be expressed as:

$$\alpha^{OAR} \cdot f_j \cdot x_j + \alpha^{NORMAL} \cdot y_j + \alpha^{TARGET} \cdot (u_z + o_z) \quad (2)$$

$$u_z = LB_z - z_j \text{ where } LB_z > z_j \quad (3)$$

$$o_z = z_j - UB_z \text{ where } UB_z < z_j \quad (4)$$

where $z_j$ is the computed dose delivered to target voxels, $LB_z$ is the lower bound of a therapeutic dose to be delivered to the target voxels, $UB_z$ is the upper bound of the therapeutic dose to be delivered to the target voxels and $\alpha^{TARGET}$ is a constant for the target voxels. The term $u_z$ represents an underdose to the target voxels, for those target voxels where $LB_z > z_j$. An underdose to the target voxels is not desired, in order to kill all tumor cells in the target voxels. The term $o_z$ represents an overdose to the target voxels, for those target voxels where $z_j > UB_z$. An overdose to the target voxels is also not desired, as it reduces uniformity of the dose delivered to the target voxels. Although equation (2) indicates that the same constant $\alpha^{TARGET}$ is used for the overdose and underdose, the constant $\alpha^{TARGET}$ is optional for either of the overdose and underdose. Additionally, different constants may be used for the overdose and underdose. Additionally, although equations (1) and (2) show the objective function in a linear formulation, this is merely one example in which the objective function can be written. In another embodiment, the objective function can be written in any formulation of the planning problem, such as a quadratic objective function.

In step 518, an irradiation plan is solved that minimizes the objective function defined above in equation (1) or (2) subject to constraints that the total dosage at each voxel 122 is within certain lower and upper bounds for the tissue type associated with the voxel 122 and for one or more uncertainty scenarios caused by subject 190 movement phases. These constraints and uncertainty scenarios are expressed as:

$$x_j = \Sigma_i w_i \cdot D_{i,j,k} \cdot p(k) \text{ for } j \in OAR \quad (5)$$

$$y_j = \Sigma_i w_i \cdot D_{i,j,k} \cdot p(k) \text{ for } j \in N \quad (6)$$

$$z_j = \Sigma_i w_i \cdot D_{i,j,k} \cdot p(k) \text{ for } j \in T \quad (7)$$

$$LB_x < x_j < UB_x \quad (8)$$

$$LB_y < y_j < UB_y \quad (9)$$

$$LB_z < z_j < UB_z \quad (10)$$

where $w_i$ is the weight for the beamlet directed at an $i^{th}$ direction from the radiation source 170 to the $j^{th}$ voxel, which are solved for by minimizing the objective function, and $D_{i,j,k}$ are dose matrices for the beamlet directed at the $i^{th}$ direction to the $j^{th}$ voxel under scenario k. The dose matrices are calculated beforehand as input to the optimization, as discussed in Ref. Phys. Med Biol. 1999 44(11):R99; 155, *Dose calculations from external photon beams in radiotherapy*, Ahnnesio A. Aspradakis, M M, which is incorporated by reference herein. In step 518, for each voxel 122, the weight $w_i$ for each beamlet directed at the voxel 122 is determined, based on the value of the utility measure $f_j$ for that voxel 122.

In an example embodiment, for those voxels 122 of the OAR that have high utility, the value of the utility measure $f_j$ is relatively high and thus the weight $w_i$ of each beamlet directed at the voxel 122 will be relatively low, in order to minimize the overall term $\alpha^{OAR} * f_j * x_j$ in equation (1) for that voxel 122.

P(k) is the probability that the tissue type within each voxel 122 will remain unchanged over various uncertainty scenarios (k), such as breathing of the subject 190. As previously discussed in step 508, the probability curves are obtained based on one or more movement phases of the subject 190 and is used to determine the probability that the tissue type within each voxel 122 will remain unchanged over the movement phases of the subject 190. In an example embodiment, in equation (2), the probability p(k) represents the probability that OAR tissue will remain within the voxel 122 over the movement phases of the subject 190, whereas in equation (3) the probability p(k) represents the probability that normal tissue will remain within the voxel 122 over the movement phases of the subject 190.

The $LB_x$ and $UB_x$ are the respective lower bound and upper bound of the computed radiation dose $x_j$ for the OAR voxels 122. The $LB_y$ and $UB_y$ are the respective lower bound and upper bound of the computed radiation dose $y_j$ for the normal tissue voxels 122. As previously discussed, the $LB_z$ and $UB_z$ are the respective lower bound and upper bound of the therapeutic radiation dose for the target voxels 122. The radiation dose delivered to the OAR voxels 122 is lower than the radiation dose delivered to the normal tissue voxels 122, which is in turn lower than the radiation dose delivered to the target voxels 122. Thus, the lower bound $LB_x$ is less than the lower bound $LB_y$, which is less than the lower bound $LB_z$. Similarly, the upper bound $UB_x$ is less than the upper bound $UB_y$, which is in turn lower than the upper bound $UB_z$.

In step 520, the radiation source 170 is operated according to the irradiation plan solved in step 518. As depicted in FIG. 4, the shape or direction of the beam 172 from the radiation source 170 is controlled at each voxel 122 by selectively positioning rectangles at various locations within a head of the radiation source 170. The intensity of the beam 172 from the radiation source 170 is adjustable and may be delivered to each voxel 122 at selective intensities over selective time intervals. In an example embodiment, the control process 140 within the computer system 150 solves for the irradiation plan in step 518. In step 520, the computer system 150 transmits signals to the radiation source 170 according to the irradiation plan. In an example embodiment, the computer system 150 transmits signals to the radiation source 170 such that the intensity and shape of the beam 172 at each voxel 122 in the OAR 194 minimizes the radiation dose delivered to high utility regions of the OAR 194.

2. Example Embodiments

FIG. 9A is a block diagram that illustrates a scanned image 902 that is similar to the scanned image 206 of FIG. 2C. The scanned image 902 identifies multiple contour lines 920 of radiation dose levels that were generated according to a conventional radiotherapy plan. As previously discussed, the conventional radiotherapy plan provides equal weight to all regions of the lung 940 when determining the contour lines 920 for the target region 930 and thus does not account for regions of different utility measurement within the lung 940. The multiple contour lines 920 within a high utility region 910 of the lung 940 include a high radiation dose of 49.5 Gray (Gy). FIG. 9B is a block diagram that illustrates a scanned image 904 that identifies contour lines 950 of radiation dose levels that are generated according to the irradiation plan of step 518. The contour lines 950 within the high utility region 910 of the lung 940 has a reduced number of high radiation dose contour lines, relative to the contour lines 920 of FIG. 9A generated according to a conventional radiotherapy plan.

Specifically, the contour line corresponding to a high radiation dose of 49.5 Gray (Gy) that is present within the high utility region 910 of the lung 940 in FIG. 9A has been shifted out of the high utility region 910 in FIG. 9B, according to the irradiation plan of step 518. As a result, the high utility region 910 of the lung 940 is spared from this high radiation dose, due to the irradiation plan of step 518 which takes into account utility measurements of the lung.

Figure 10A:
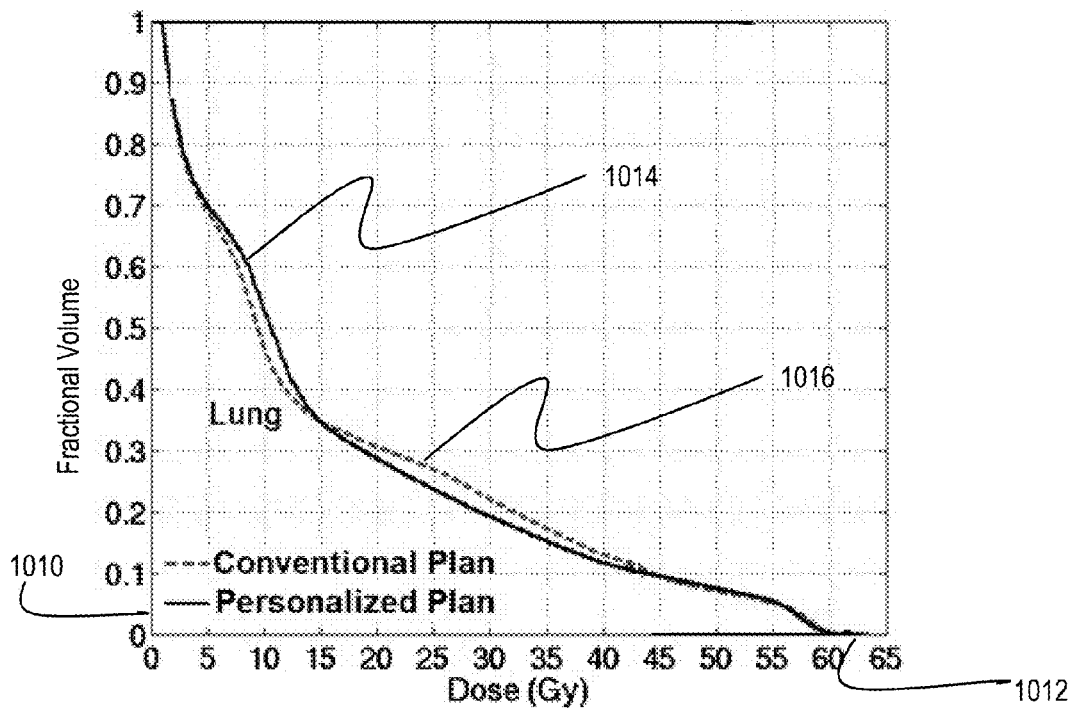
FIG. 10A illustrates an example of a dose-volume histogram (DVH) of the conventional plan and the plan according to an embodiment for irradiation therapy.

FIG. 10A illustrates an example of a dose-volume histogram (DVH) 1016 of the conventional plan and a DVH 1014 of the plan determined in step 518. The horizontal axis 1012 is the radiation dose in units of Gray (Gy). The vertical axis 1010 is a unitless fractional volume of the lungs which have a minimum dosage of radiation, according to each plan. For example, the DVH 1016 indicates a fractional volume of 0.3 at a minimum dose of 20 Gy, which indicates that 30% of the lung volume has a dose of 20 Gy or more, according to the conventional radiation plan. Based on FIG. 10A, a greater number of lung voxels 122 have a low dose (<15 Gy) in the irradiation plan determined in step 518 than the conventional radiation plan. However, a reduced number of lung voxels 122 have a high dose (>15 Gy) in the irradiation plan determined in step 518 than the conventional radiation plan.

Figure 10B:
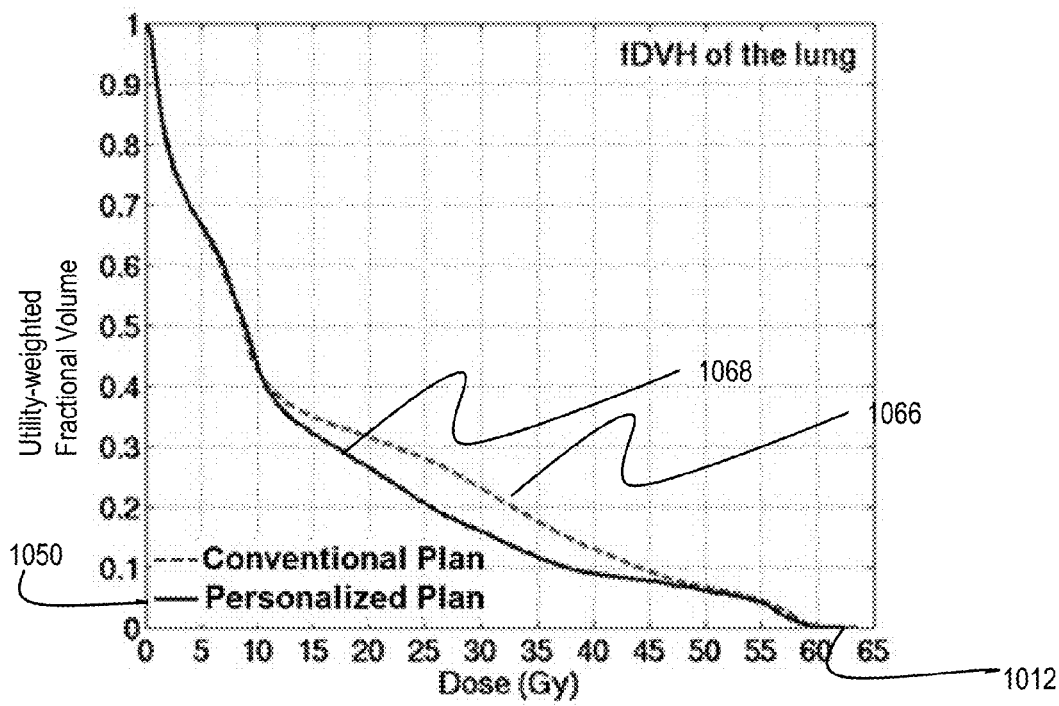
FIG. 10B illustrates an example of a functional dose-volume histogram (fDVH) of the conventional plan and the plan according to an embodiment for irradiation therapy.

FIG. 10B illustrates an example of a functional dose-volume histogram (fDVH) 1066 of the conventional plan and a fDVH 1068 of the plan determined in step 518. The horizontal axis 1012 is the radiation dose in units of Gray (Gy). The vertical axis 1050 is a unit less utility-weighted fractional volume of the lungs, which is based on a product of the fractional volume of the lungs which has a minimum dosage of radiation, multiplied by the utility measure $f_j$ of the voxels in the fractional volume of the lungs, according to each plan. As depicted in FIGS. 8A-8C, the plan determined in step 518 involves increased sparing of high utility regions of the lung from high radiation dosage than the conventional radiotherapy plan which does not consider utility measurements of the lung. Thus, in the fDVH 1066, 1068 of FIG. 10B, where lung voxels 122 of high utility are weighed more than voxels 122 of low utility, the gap between the fDVH 1068 of the plan determined in step 518 and the fDVH 1066 of the conventional plan is even more pronounced for high dose (>15 Gy) than between the DVH 1014, 1016 of FIG. 10A.

Figure 11:
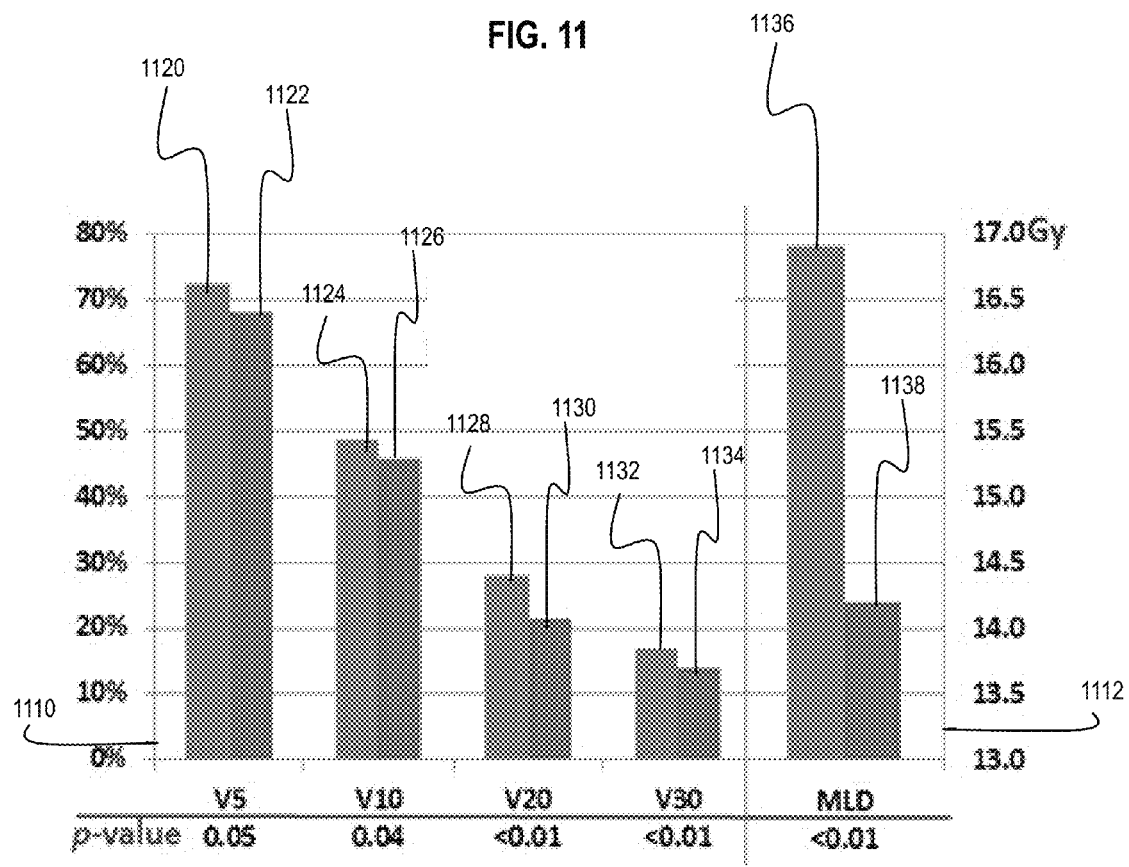
FIG. 11 is a bar chart that illustrates examples of percentages of the OAR voxels receiving various radiation dosages and an example of the OAR average radiation dosage in the conventional plan and plan according to an embodiment for irradiation therapy.

FIG. 11 is a bar chart that illustrates examples of percentages of the OAR voxels receiving various radiation dosages in the conventional plan and plan according to an embodiment for irradiation therapy. The left vertical axis 1110 is the fractional volume of the lungs which have a minimum dosage of radiation. As illustrated in FIG. 11, a fractional volume 1120 above 70% of the lungs had a minimum dosage of 5 Gy, according to the conventional plan, whereas a fractional volume 1122 less than 70% of the lungs had the minimum dosage of 5 Gy, according to the plan determined in step 518. As illustrated in FIG. 11, a fractional volume 1124 of approximately 50% of the lungs had a minimum dosage of 10 Gy, according to the conventional plan, whereas a fractional volume 1126 of approximately 45% of the lungs had the minimum dosage of 10 Gy, according to the plan determined in step 518. As illustrated in FIG. 11, a fractional volume 1128 of approximately 30% of the lungs had a minimum dosage of 20 Gy, according to the conventional plan, whereas a fractional volume 1130 of approximately 20% of the lungs had the minimum dosage of 20 Gy, according to the plan determined in step 518. As illustrated in FIG. 11, a fractional volume 1132 of approximately 15% of the lungs had the minimum dosage of 30 Gy, according to the conventional plan, whereas a fractional volume 1134 of approximately 12% of the lungs had the minimum dosage of 20 Gy, according to the plan determined in step 518.

FIG. 11 is a bar chart that illustrates an example of the mean lung dose (MLD) in the conventional plan and plan according to an embodiment for irradiation therapy. The right vertical axis 1112 is a dosage of the lung in units of Gray (Gy). As illustrated in FIG. 11, a MLD 1136 of the lung voxels in the conventional plan is approximately 17.0 Gy, whereas a MLD 1138 of the lung voxels in the plan determined in step 518 is approximately 14.0 Gy.

Thus, FIG. 11 shows that at each dose level the utility weighted plan irradiates fewer high functioning lung pixels and thus a lower high functioning lung volume. The difference is statistically significant.

3. Hardware Overview

FIG. 12 is a block diagram that illustrates a computer system ~00 upon which an embodiment of the invention may be implemented. Computer system ~00 includes a communication mechanism such as a bus 1210 for passing information between other internal and external components of the computer system 1200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing one or more steps of one or more methods described herein.

A sequence of binary digits constitutes digital data that is used to represent a number or code for a character. A bus 1210 includes many parallel conductors of information so that information is transferred quickly among devices coupled to the bus 1210. One or more processors 1202 for processing information are coupled with the bus 1210. A processor 1202 performs a set of operations on information. The set of operations include bringing information in from the bus 1210 and placing information on the bus 1210. The set of operations also typically include comparing two or more units of information, shifting positions of units of information, and combining two or more units of information, such as by addition or multiplication. A sequence of operations to be executed by the processor 1202 constitutes computer instructions.

Computer system 1200 also includes a memory 1204 coupled to bus 1210. The memory 1204, such as a random access memory (RAM) or other dynamic storage device, stores information including computer instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of computer instructions. The computer system 1200 also includes a read only memory (ROM) 1206 or other static storage device coupled to the bus 1210 for storing static information, including instructions, that is not changed by the computer system 1200. Also coupled to bus 1210 is a non-volatile (persistent) storage device 1208, such as a magnetic disk or optical disk, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into signals compatible with the signals used to represent information in computer system 1200. Other external devices coupled to bus 1210, used primarily for interacting with humans, include a display device 1214, such as a cathode ray tube (CRT) or a liquid crystal display (LCD), for presenting images, and a pointing device 1216, such as a mouse or a trackball or cursor direction keys, for controlling a position of a small cursor image presented on the display 1214 and issuing commands associated with graphical elements presented on the display 1214.

In the illustrated embodiment, special purpose hardware, such as an application specific integrated circuit (IC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1270 sends and receives electrical, acoustic or electromagnetic signals, including infrared and optical signals, that carry information streams, such as digital data.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1202, except for carrier waves and other signals.

Logic encoded in one or more tangible media includes one or both of processor instructions on a computer-readable storage media and special purpose hardware, such as ASIC *1220.

Network link 1278 typically provides information communication through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290. A computer called a server 1292 connected to the Internet provides a service in response to information received over the Internet. For example, server 1292 provides information representing video data for presentation at display 1214.

The invention is related to the use of computer system 1200 for implementing the techniques described herein. According to one embodiment of the invention, those techniques are performed by computer system 1200 in response to processor 1202 executing one or more sequences of one or more instructions contained in memory 1204. Such instructions, also called software and program code, may be read into memory 1204 from another computer-readable medium such as storage device 1208. Execution of the sequences of instructions contained in memory 1204 causes processor 1202 to perform the method steps described herein. In alternative embodiments, hardware, such as application specific integrated circuit 1220, may be used in place of or in combination with software to implement the invention. Thus, embodiments of the invention are not limited to any specific combination of hardware and software.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server 1292 transmits program code for a particular application, requested by a message sent from computer 1200, through Internet 1290, ISP equipment 1284, local network 1280 and communications interface 1270. The received code may be executed by processor 1202 as it is received, or may be stored in storage device 1208 or other non-volatile storage for later execution, or both. In this manner, computer system 1200 may obtain application program code in the form of a signal on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red a carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

FIG. 13 illustrates a chip set 1300 upon which an embodiment of the invention may be implemented. Chip set 1300 is programmed to perform one or more steps of a method described herein and includes, for instance, the processor and memory components described with respect to FIG. *12 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1300, or a portion thereof, constitutes a means for performing one or more steps of a method described herein.

In one embodiment, the chip set 1300 includes a communication mechanism such as a bus 1301 for passing information among the components of the chip set 1300. A processor 1303 has connectivity to the bus 1301 to execute instructions and process information stored in, for example, a memory 1305. The processor 1303 may include one or more processing cores with each core configured to perform independently. A multi-core processor enables multiprocessing within a single physical package. Examples of a multi-core processor include two, four, eight, or greater numbers of processing cores. Alternatively or in addition, the processor 1303 may include one or more microprocessors configured in tandem via the bus 1301 to enable independent execution of instructions, pipelining, and multithreading. The processor 1303 may also be accompanied with one or more specialized components to perform certain processing functions and tasks such as one or more digital signal processors (DSP) 1307, or one or more application-specific integrated circuits (ASIC) 1309. A DSP 1307 typically is configured to process real-world signals (e.g., sound) in real time independently of the processor 1303. Similarly, an ASIC 1309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1303 and accompanying components have connectivity to the memory 1305 via the bus 1301. The memory 1305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1305 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method comprising:
    determining size and location of each voxel of a plurality of voxels in a reference frame of a radiation device that emits a beam of radiation with controlled intensity and beam cross sectional shape
    obtaining first measurements that relate to tissue type inside a subject at each voxel of the plurality of voxels based on a first imaging device;
    obtaining different second measurements that relate to utility of tissue type inside the subject at each voxel of the plurality of voxels based on a second imaging device;
    determining a first subset of the plurality of voxels, wherein the first subset encloses a target volume to be irradiated with a therapeutic dose of radiation by the radiation device;
    determining a second subset of the plurality of voxels, wherein the second subset encloses an organ-at-risk (OAR) volume;
    determining on a processor a value of a utility measure $fj$ at each voxel of the second subset based on the a corresponding value of the second measurements
    determining on a processor a series of beam shapes and intensities from the radiation device which minimize a value of an objective function that is based on a computed dose delivered to an OAR voxel multiplied by the utility measure $fj$ for that voxel summed over all voxels; and
    controlling the radiation device to deliver the series of beam shapes and intensities.

2. A method as recited in claim 1 wherein the first imaging device is one of an X-ray Computed tomography (CT) scanner or an nuclear magnetic resonance imagery (MRI) scanner.

3. A method as recited in claim 1 wherein the second imaging device is one of a positron emission tomography (PET) scanner, a Single photon emission computed tomography (SPECT) scanner, a functional magnetic resonance imager (fMRI) or a four-dimensional computed tomography (4DCT)-based ventilation imaging system.

4. A method as recited in claim 1 wherein the utility measure $f_j$ is based on a piecewise linear cumulative distribution of the second measurements.

5. A method as recited in claim 4 wherein the piecewise linear cumulative distribution of the second measurements includes a constant maximum values of $fj$ for values of the second measurements above a peak in a histogram of the values of the second measurements.

6. A method as recited in claim 1 wherein the OAR is a lung within the subject.

7. A method as recited in claim 1 wherein each voxel has a length in a range of 3-5 millimeters, a width in a range of 3-5 millimeters and a depth in a range of 2-3 millimeters.

8. A method as recited in claim 1 wherein each voxel associated with a tissue type also has an associated probability based on expected movement of the tissue type out of the voxel during the irradiation therapy.

9. A computer-readable medium carrying one or more sequences of instructions, wherein execution of the one or more sequences of instructions by one or more processors causes the one or more processors to perform the steps of:
    receiving first measurements from a first imaging device that relate to tissue type inside a subject at each voxel of a plurality of voxels;
    receiving different second measurements from a second imaging device that relate to utility of tissue type inside the subject at each voxel of the plurality of voxels;
    determining a value of a utility measure $fj$ at each voxel of a subset of the plurality of voxels that enclose an organ-at-risk (OAR) volume inside the subject based on a corresponding value of the second measurements;
    determining a series of beam shapes and intensities from a radiation device which minimize a value of an objective function that is based on a computed dose delivered to an OAR voxel multiplied by the utility measure $fj$ for that voxel summed over all voxels; and
    controlling the radiation device to deliver the series of beam shapes and intensities.

10. A system comprising:
    a radiation device to emit a beam of radiation with controlled intensity and beam cross sectional shape in each voxel of a plurality of voxels in a reference frame of the radiation device;
    one or more imaging devices to obtain one or more measurements that relate to tissue type inside a subject at each voxel of the plurality of voxels;
    at least one processor; and
    at least one memory including one or more sequence of instructions;
    the at least one memory and the one or more sequence of instructions configured to, with the at least one processor, cause the at least one processor to receive the one or more measurements from the one or more imaging devices, to determine a value of a utility measure $f_j$ at each voxel of a subset of the plurality of voxels that enclose an organ-at-risk (OAR) volume inside the subject based on a corresponding value of the one or more measurements, to determine the controlled intensity and beam cross sectional shape in each voxel that minimize a value of an objective function that is based on a computed dose delivered to an OAR voxel multiplied by the utility measure $f_j$ for that voxel summed over all voxels and to control the radiation device to deliver the series of beam shapes and intensities.

11. A system as recited in claim 10 wherein the imaging device is one of an X-ray Computed tomography (CT) scanner or an nuclear magnetic resonance imagery (MRI) scanner.

12. A system as recited in claim 10 wherein the imaging device is one of a positron emission tomography (PET)

scanner, a Single photon emission computed tomography (SPECT) scanner, a functional magnetic resonance imager (fMRI) or a four-dimensional computed tomography (4DCT)-based ventilation imaging system.

13. A system as recited in claim 10 wherein the utility measure $f_j$ is based on a piecewise linear cumulative distribution of the measurements.

14. A system as recited in claim 13 wherein the piecewise linear cumulative distribution of the second measurements includes a constant maximum values of $fj$ for values of the second measurements above a peak in a histogram of the values of the second measurements.

15. A system as recited in claim 10 wherein the OAR is a lung within the subject.

16. A system as recited in claim 10 wherein each voxel has a length in a range of 3-5 millimeters, a width in a range of 3-5 millimeters and a depth in a range of 2-3 millimeters.

* * * * *